(12) United States Patent
Cevc et al.

(10) Patent No.: US 7,820,720 B2
(45) Date of Patent: Oct. 26, 2010

(54) TOPICAL TERBINAFINE FORMULATIONS AND METHODS OF ADMINISTERING SAME FOR THE TREATMENT OF FUNGAL INFECTIONS

(75) Inventors: Gregor Cevc, Gauting (DE); Ulrich Vierl, Groebenzell (DE)

(73) Assignee: TDT Limited, Valletta (MT)

( * ) Notice: Subject to any disclaimer, the term of this patent is extended or adjusted under 35 U.S.C. 154(b) by 0 days.

(21) Appl. No.: 12/689,470

(22) Filed: Jan. 19, 2010

(65) Prior Publication Data

US 2010/0104633 A1    Apr. 29, 2010

Related U.S. Application Data

(63) Continuation of application No. 12/508,537, filed on Jul. 23, 2009.

(60) Provisional application No. 61/083,115, filed on Jul. 23, 2008, provisional application No. 61/102,111, filed on Oct. 2, 2008, provisional application No. 61/150,187, filed on Feb. 5, 2009, provisional application No. 61/168,122, filed on Apr. 9, 2009.

(51) Int. Cl.
| | |
|---|---|
| *A01N 33/02* | (2006.01) |
| *A01N 33/24* | (2006.01) |
| *A61K 31/135* | (2006.01) |
| *A61K 31/13* | (2006.01) |
| *A61K 9/20* | (2006.01) |
| *A61K 9/14* | (2006.01) |

(52) U.S. Cl. .............. 514/657; 514/655; 424/464; 424/484; 424/489

(58) Field of Classification Search ............. 514/657, 514/655; 424/464, 484, 489
See application file for complete search history.

(56) References Cited

U.S. PATENT DOCUMENTS

| | | | |
|---|---|---|---|
| 6,121,314 | A | 9/2000 | Richter et al. |
| 6,623,753 | B1 | 9/2003 | Bodmer et al. |
| 2004/0105881 | A1 | 6/2004 | Cevc et al. |
| 2006/0110342 | A1 | 5/2006 | Dechow |
| 2008/0188568 | A1 | 8/2008 | Suvanprakorn et al. |

FOREIGN PATENT DOCUMENTS

| | | | |
|---|---|---|---|
| WO | WO 02/078648 | A2 | 10/2002 |
| WO | WO 2005/087195 | A2 | 9/2005 |

OTHER PUBLICATIONS

U.S. Appl. No. 60/899,433, filed Feb. 5, 2007.
International Search Report and Written Opinion of the International Searching Authority for International Application No. PCT/IB2009/006742, mailed Dec. 23, 2009.

*Primary Examiner*—Frederick Krass
*Assistant Examiner*—Benjamin Packard
(74) *Attorney, Agent, or Firm*—Jones Day

(57) ABSTRACT

The present invention relates to topical antifungal formulations terbinafine or a pharmaceutically acceptable salt thereof, a lipid, and a surfactant, and uses thereof for the treatment of skin and nail fungal infections.

20 Claims, No Drawings

TOPICAL TERBINAFINE FORMULATIONS AND METHODS OF ADMINISTERING SAME FOR THE TREATMENT OF FUNGAL INFECTIONS

PRIORITY

This application is a continuation of U.S. patent application Ser. No. 12/508,537, filed Jul. 23, 2009, which itself claims the benefit of U.S. Provisional Application No. 61/083,115, filed Jul. 23, 2008, U.S. Provisional Application No. 61/102,111, filed Oct. 2, 2008, U.S. Provisional Application No. 61/150,187, filed Feb. 5, 2009, and U.S. Provisional Application No. 61/168,122, filed Apr. 9, 2009. The contents of each of these applications is hereby incorporated by reference herein their entirety.

1. FIELD OF INVENTION

The present invention relates to topical formulations of an antifungal comprising one or more antifungals, a lipid and a surfactant, and uses thereof for the treatment of skin and nail fungal infections.

2. BACKGROUND

Onychomycosis is a fungal infection of the fingernails and toenails that results in thickening, discoloration, splitting of the nails and lifting of the nails from the nail bed. The disease is caused by dermophytes and has a high incidence within the general population, especially among older individuals. Onychomycosis is most commonly caused by *Trichophyton rubrum* (*T. rubrum*), *Trichophyton mentagrophytes* (*T. mentagrophytes*), and *Epidermophyton floccusum* (*E. floccusum*). Onychomycosis due to nondermatophytes is usually caused by *Candida* species, such as *Candida albicans*, and is more likely to cause invasive nail disease in fingernails than in toenails of immunocompetent individuals.

Rates of onychomycosis vary with the population considered. A recent study of the general United States population revealed a prevalence of 2% to 3%, while a study reported in Finland reported a rate of 13% (Elewski et. al., J. Am. Acad. Dermatol. 2000; 42(1)(Pt 1): 1-20, and Heikkila et. al., Br. J. Dermatol. 1995; 133(5): 699-703). Onychomycosis may affect up to about 15% of persons between the ages of 40 and 60 years (Kepka et. al. U.S. Patent Pub. No. 2006/0067898).

Terbinafine is an antimycotic currently indicated as an oral therapy for the treatment of onychomycosis (Lamisil™, Novartis International AG, Basel, Switzerland). Other treatment options including chemical or surgical removal of the infected nail(s) can lead to nail bed shrinkage and dorsal dislocation of the nail bed.

Citation of any reference in this section of the application is not an admission that the reference is prior art to the application.

3. SUMMARY OF THE INVENTION

The present invention provides topical formulations of one or more antifungals, which may be used to treat fungal infections in a human subject. The topical antifungal formulations of the invention comprise one or more antifungals and one or more lipids and one or more surfactants in a pharmaceutically acceptable carrier. In certain embodiments, the antifungal is terbinafine, salts of terbinafine, or derivatives or analogs of terbinafine, either alone or in combination with one or more antifungals. In certain embodiments, the antifungal is abafungin, acrisorcin, albaconazole, albendazole, amorolfine, amphotericin B, anidulafungin, arasertaconazole, azithromycin, becliconazole, benzodithiazole, bifonazole, butoconazole, butenafine, calbistrin, caspofungin, N-chlorotaurine, chloroxine, chlorphenesin, ciclopirox, cioteronel, clotrimazole, croconazole, cytoporins, deoxymulundocandin, eberconazole, econazole, efungumab, fenticonazole, flavanoid glycosides, fluconazole, flucytosine, flutrimazole, fosfluconazole, genaconazole, gentian violet, griseofulvin, griseofulvin PEG, haloprogin, hydroxy itraconazole, isoconazole, itraconazole, ketoconazole, lanoconazole, letrazuril, liranaftate, luliconazole, micafungin, miconazole, mycophenolic acid, naftifine, natamycin, nitazoxanide, nitro-ethylene based antifungals, nystatin, omocanazole, oxiconazole, polyene macrolide, polyene macrolide, posaconazole, pramiconazole, quinolone analogs, rapamycin, ravuconazole, rilopirox, samidazole, sertaconazole, sitamaquine, sordaricin, squalestatin, squalene, a squalene epoxidase inhibitor, sulconazole, sultriecin, tafenoquine, terconazole, tioconazole, tolnaftate, voriconazole, or a compound of Formula I:

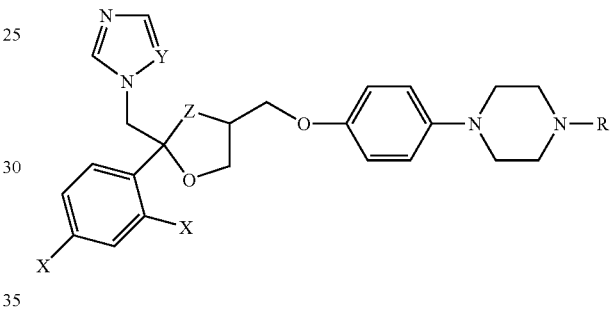

(I)

or a single enantiomer, a mixture of enantiomers, or a mixture of diastereomers thereof; or a pharmaceutically acceptable solvate, hydrate, or salt thereof; where R is $C_{1-12}$ alkyl, $C_{1-12}$ acyl, or heteroaryl-$C_{6-14}$ aryl; X is halo; Y is N or CH; and Z is $CH_2$ or O. In certain embodiments, the topical antifungal formulations of the invention comprise terbinafine, one or more phospholipids and one or more nonionic surfactants. In certain embodiments, the topical antifungal formulations of the invention comprise terbinafine and an additional antifungal, one or more phospholipids and one or more nonionic surfactants. In certain embodiments, the topical antifungal formulations provided herein comprise one of itraconazole, ketoconazole, posaconazole, saperconazole, SCH-50002, terconazole, butenafine, and griseofulvin; and hydrates, solvates, and salts thereof; one or more phospholipids, and one or more nonionic surfactants. In certain embodiments, the antifungal formulations provided herein comprise an antifungal agent that is from a class of antifungal agents that include, bur are not limited to, antimetabolites, macrolides, echinocadins, imidazoles, triazoles, benzylamines, griseofulvins, allylamines, polyenes, thiocarbamates, and halogenated phenol ethers. The disclosure relates to topical formulations, such as solutions, suspensions, gels, fluid gels, emulsions, emulsion gels, lotions, ointments, film forming solutions, creams, sprays and lacquers.

In particular, the antifungal formulations of the invention may be used to treat or prevent onychomycosis in a human subject. The antifungal formulations of the invention may also be used to treat or prevent fungal infections of the skin including, but not limited to tinea corporis, tinea cruris, tinea pedis, pityriasis (tinea) versicolor. The antifungal formulations of the invention may also be used to treat fungal infections commonly caused by *Trichophyton* (e.g., *T. rubru, T. mentagrophytes, T. verrucosum, T. violaceum*), *Microsporum canis*, *Epidermophyton floccusum* (*E. floccusum*) and yeasts of the genus *Candida* (e.g., *Candida albicans*), as well as *Malassezia furfur*.

The antifungal formulations of the invention facilitate the delivery of antifungal to the infected area in an amount sufficient to treat the fungal infection. In the case of onychomycosis, the formulation can be administered to the nail and/or the surrounding skin. The formulation may also be administered to the entire toe and/or finger tip. The formulation may preferably be administered to the distal phalanx of the finger or toe. In the case of skin infection, the formulation can be administered to the infected area of the skin. In one embodiment, the topical terbinafine formulation is applied to the surface of the nail (i.e., the nail plate) and to the skin surrounding the nail. In another embodiment, the topical terbinafine formulation is applied epicutaneously.

In one embodiment, provided herein is a method for treating onychomycosis comprising topically administering to a subject, a pharmaceutical formulation comprising a therapeutically effective amount of one or more antifungals as described herein, e.g., terbinafine, a lipid, preferably a phospholipid, and a surfactant, preferably a nonionic surfactant. In another embodiment, the invention encompasses a method for the delivery of antinfungal to the nail in an amount effective for treating onychomycosis comprising topically administering to a subject a pharmaceutical formulation comprising one or more antifungals as described herein, e.g., terbinafine, a lipid and a surfactant. In some embodiments, the method comprises administering to a subject the topical antifungal formulations as described herein in combination with a second antifungal formulation (either topically administered or otherwise).

Provided herein is a regimen for the treatment of onychomycosis in a human subject comprising the administration of a composition comprising an antifungal, e.g., terbinafine, a lipid and a surfactant to an infected nail and/or to the skin tissue surrounding the infected nail. The composition is to be administered for a period of time spanning two or more weeks, including three, four, five, six, seven, eight, nine, ten, eleven, twelve weeks or more. In one embodiment, the composition is to be administered for a period of ten to twelve weeks. The composition is to be administered for a period of time to result in a mycological cure rate, preferably greater than about 70%, 75%, 80%, 85%, 90%, 95%, 96%, 97%, 98%, or 99% in the infected nail in the human subject.

As used herein, the terms "treat", "treating" or "treatment of" mean that the severity of a subject's condition is reduced or at least partially improved or ameliorated and/or that some alleviation, mitigation or decrease in at least one clinical symptom is achieved and/or there is an inhibition or delay in the progression of the condition and/or delay in the progression of the onset of disease or illness. The terms "treat", "treating" or "treatment of" also means managing the disease state, e.g., onychomycosis.

The degree of treatment of onychomycosis in a subject may be measured by the mycological cure rate. The mycological cure rate is defined by negative microscopy of nail samples and negative culture for dermatophytes in nails treated with an antifungal.

Another way to determine the success of a treatment is by measuring the clinical cure rate. The clinical cure rate may be defined by normal growth of toe nail of at least 2 mm after 24 weeks and 5 mm after 48 weeks according to published methods (Tavakkol, et. al. The American Journal of Geriatric Pharmacotherapy. 2006; 4: 1-13).

In one embodiment, the topical formulation is administered to nail tissue and/or surrounding skin of a human subject to achieve a mean concentration of the antifungal per gram of nail tissue of from about 1 mg/g to about 50 mg/g, from about 1 mg/g to about 25 mg/g, from about 1 mg/g to about 5 mg/g, or from about 1 mg/g to about 10 mg/g. In another embodiment, the topical formulation is administered to nail tissue and/or surrounding skin of a human subject to achieve a mean concentration of the antifungal per gram of nail tissue of at least 1.5 mg/g, 2.0 mg/g, 2.1 mg/g, 2.2 mg/g, 2.3 mg/g, 2.4 mg/g, 2.5 mg/g, 2.6 mg/g, 2.7 mg/g, 2.8 mg/g, 2.9 mg/g, 3.0 mg/g, 5 mg/g, 10 mg/g. 15 mg/g, 20 mg/g, 25 mg/g, 30 mg/g. 35 mg/g, 40 mg/g, 45 mg/g, or 50 mg/g. In yet another embodiment, the topical formulation is administered to nail tissue and/or surrounding skin of a human subject to achieve a mean concentration of the antifungal per gram of nail tissue of about 0.1 to about 15 mg/g; about 0.2 to about 12.5 mg/g, about 0.5 to about 10 mg/g, about 1 to about 7.5 mg/g, or about 2 to about 5 mg/g. The mean concentration may be determined one, two or three weeks after ceasing administration of the topical formulation.

In certain embodiments of the methods, the administration of topical antifungal formulations of the invention also results in a mean serum concentration of terbinafine in the human subject of less than 10.0 ng/ml, 5.0 ng/ml, 4.0 ng/ml, 3.0 ng/ml, 2.0 ng/ml, 1.0 ng/ml, 0.5 ng/ml or 0.2 ng/ml.

In some embodiments of the method, the topical formulation comprises about 3.0 mg of terbinafine. The topical formulation can be administered, for example, twice daily. In certain embodiments, the topical formulation is administered for at least three weeks.

In another aspect, the invention provides a method of administering a topical formulation comprising terbinafine, a lipid, and a surfactant, wherein the method comprises administering the topical formulation to nail tissue twice daily for at least one, two or three weeks.

In some embodiments of the method, the topical formulation comprises from about 0.1 to about 5.0 mg, preferably 1.0 to about 5.0 mg of terbinafine. For instance, the topical formulation can comprise about 3.0 mg of terbinafine.

In some embodiments of the method, the terbinafine in the topical formulation is in salt form.

In another aspect, the invention provides a method of treating a fungal infection of nail tissue in a human subject comprising administering a pharmaceutical composition to the infected nail tissue of the human subject to target a mean concentration of terbinafine per gram of nail tissue of about 0.1 to about 15 mg/g, about 0.2 to about 12.5 mg/g, about 0.5 to about 10.0 mg/g, about 1.0 to about 7.5 mg/g or about 2.0 to about 5.0 mg/g. The mean concentration can be determined one, two or three weeks after ceasing administration of the pharmaceutical composition. The administration also results in a mean serum concentration of terbinafine in the human subject of less than 10 ng/mL, 5.0 ng/ml, 4.0 ng/ml, 3.0 ng/ml, 2.0 ng/ml, 1.0 ng/ml, 0.5 ng/ml or 0.2 ng/ml. The pharmaceutical composition comprises terbinafine, a lipid, and a surfactant.

In some embodiments of the method, the topical formulation comprises from about 1 to about 20 mg of the antifungal. In some embodiments of the method, the topical formulation comprises about 1 mg, about 2 mg, about 3 mg, about 4 mg, about 5 mg, about 8 mg, about 10 mg, about 12 mg, about 14 mg, about 16 mg, about 18 mg, or about 20 mg of the antifungal. The topical formulation can be administered, for example, once or twice daily. In certain embodiments, the topical formulation is administered for at least three weeks.

In some embodiments of the method, the lipid in the pharmaceutical composition is a phospholipid.

In certain embodiments of the method, the antifungal in the pharmaceutical composition is in salt form. In certain embodiments, a certain portion of the antifungal in the pharmaceutical composition is in salt form.

In another aspect, the invention provides a method of treating a fungal infection of nail tissue in a human subject comprising administering a pharmaceutical composition to the infected nail tissue of the human subject twice daily for at least three weeks, wherein the pharmaceutical composition comprises an antifungal, a lipid, and a surfactant.

In some embodiments of the method, the pharmaceutical composition comprises from about 1 to about 20 mg of the antifungal. For instance, the pharmaceutical composition can comprise about 1, about 2, about 3, about 4, about 5, about 6, about 7, about 8, about 9, about 10, about 11, about 12, about 13, about 14, about 15, about 16, about 17, about 18, about 19, or about 20 mg of the antifungal.

In certain embodiments of the method, the lipid in the pharmaceutical composition is a phospholipid.

In some embodiments of the method, the terbinafine in the pharmaceutical composition is in salt form.

Further provided herein is a regimen for the treatment of onychomycosis in a human subject comprising the administration of a pharmaceutically acceptable formulation comprising an antifungal as described herein, e.g., terbinafine, a lipid, preferably a phospholipid, and a surfactant, preferably a nonionic surfactant, to an infected nail and/or to the skin surrounding the infected nail. The formulation is to be administered for a period of time, preferably spanning two or more weeks, including three, four, five, six, seven, eight, nine, ten, eleven, twelve weeks or more. In one embodiment, the formulation is to be administered for a period of ten to twelve weeks. The formulation is to be administered for a period of time to result in a mycological cure rate, preferably greater than about 70%, 75%, 80%, 85%, 90%, 95%, 96%, 97%, 98%, or 99% in the infected nail in the human subject. Alternatively, the formulation is administered for a period of time to prevent recurrence of fungal infection.

As used herein, the term "pharmaceutically acceptable" when used in reference to the formulations of the invention denotes that a formulation does not result in an unacceptable level of irritation in the subject to whom the formulation is administered. Preferably such level will be sufficiently low to provide a formulation suitable for approval by regulatory authorities.

As used herein, a "sufficient amount," "amount effective to" or an "amount sufficient to" achieve a particular result refers to an amount of terbinafine or a salt thereof that is effective to produce a desired effect, which is optionally a therapeutic effect (i.e., by administration of a therapeutically effective amount). Alternatively stated, a "therapeutically effective" amount is an amount that provides some alleviation, mitigation, and/or decrease in at least one clinical symptom. Clinical symptoms associated with the disorder that can be treated by the methods of the invention are well-known to those skilled in the art. Further, those skilled in the art will appreciate that the therapeutic effects need not be complete or curative, as long as some benefit is provided to the subject. For example, a "sufficient amount" or "an amount sufficient to" can be an amount that is effective to treat onychomycosis, may be defined as a mycological cure.

Embodiments of the invention are useful in preparations for the application, administration and/or transport of an antifungal, especially for medicinal or biological purposes, into and through barriers and constrictions, such as the skin or nail of mammalian subject (e.g., humans). As a result, the topical antifungal formulations may reach the site of infection, for example the nail bed, in amount sufficient and in physical form adequate to treat onychomycosis.

In certain embodiments, the antifungal formulations provided herein preferably form vesicles or other extended surface aggregates (ESAs), wherein the vesicular preparations have improved permeation capability through the semi-permeable barriers, such as skin and/or nails. While not to be limited to any mechanism of action, the preferred antifungal formulations are able to form vesicles characterized by their deformability and/or adaptability. The vesicles' deformability and/or adaptability allows the vesicles to penetrate the pores of the skin and/or nails and deliver antifungal to the site of infection in an amount sufficient to treat the infection. The adaptability or deformability of the vesicles may be determined by the ability of the vesicles to penetrate a barrier with pores having an average pore diameter at least 50% smaller than the average vesicle diameter before the penetration. Thus, in certain embodiments, the formulation comprises deformable vesicles capable of penetrating a barrier with pores having an average pore diameter at least 50% smaller than the average vesicle diameter before the penetration. In some embodiments, the pores are human skin pores or animal skin pores. In some embodiments, the average pore diameter is from about 10 microns to about 100 microns, about 30 to about 70 microns, or about 40 to about 60 microns.

Deformability can be assessed using the following method: 1) measure the flux ($j_a$) of the aggregate or ESA suspension through a semi-permeable membrane (e.g., gravimetrically) for different transport-driving trans barrier pressures ($\Delta p$); 2) calculate the pressure dependence of barrier penetratability P for the suspension by dividing each measured flux value by the corresponding pressure value: $P(\Delta p)=j_a(\Delta p)/\Delta p$; 3) monitor the ratio of final and starting vesicle diameter 2 $r_{ves}(\Delta p)/2$ $r_{ves,0}$ (e.g. by dynamic light scattering), wherein 2 $r_{ves}(\Delta p)$ is the vesicle diameter after semi-permeable barrier passage driven by $\Delta p$ and 2 $r_{ves,0}$ is the starting vesicle diameter, and if necessary make corrections for the flow-effects; and 4) align both data sets $P(\Delta p)$ vs. $r_{ves}(\Delta p)/r_{ves,0}$ to determine the co-existence range for high aggregate adaptability and stability.

In certain embodiments, the mycological cure rate is greater than about 70%, 75%, 80%, 85%, 90%, 95% or 99% in human subjects after about 14-weeks, 12-weeks, 10-weeks, 8-weeks, 6-weeks, 4-weeks or 2-weeks of treatment.

In certain embodiments, the clinical cure rate is greater than about 70%, 75%, 80%, 85%, 90%, 95% or 99% in human subjects after about 48-weeks, 24-weeks, 12-weeks, 10-weeks, 8-weeks, 6-weeks, 4-weeks or 2-weeks of treatment.

The amount of the antifungal administered per administration to a subject in an area affected by onychomycosis according to certain embodiments of the methods of the invention may be from about 0.25 mg to about 20.0 mg, about 0.5 mg to about 10.0 mg, about 0.5 mg to about 5.0 mg, about 1.0 mg, 2.0 mg, 3.0 mg, 4.0 mg, 5.0 mg, 6.0 mg, 7.0 mg, 8.0 mg, 9.0 mg, 10.0 mg, 11.0 mg, 12.0 mg, 13.0 mg, 14.0 mg, 15.0 mg, 16.0 mg, 17.0 mg, 18.0 mg, 19.0 mg or 20.0 mg. Such amount may be increased above 20.0 mg (e.g., to 30, 40. 50, 75 or 100 mg) if desired in any particular patient for an appropriate length of time. As used herein with respect to numerical values, the term "about" means a range surrounding a particular numeral value which includes that which would be expected to result from normal human error in making a measurement. For example, in certain embodiments, the term "about" when used in connection with a particular numerical value means±1%, ±2%, ±3%, ±4%, ±5% or ±10% of the numerical value. The antifungal formulations of the invention may be administered about once-a-day, twice-a-day, three times daily, four times daily, every two days, every three days or once weekly.

In certain embodiments for the administration of the topical antifungal formulations provided herein, the total daily dosage of the antifungal administered to a specific site infected with onychomycosis may be from about 0.25 mg to about 20 mg, from about 0.5 mg to about 5 mg, from about 5 mg to about 10 mg, from about 10 mg to about 15 mg, or from about 15 mg to about 20 mg. In specific embodiments, the daily dose of the antifungal administered to a site of infection is about 1 mg, about 1.5 mg, about 3 mg, about 6 mg, about 9 mg, or about 12 mg. In certain embodiments, the total daily dosage of the antifungal administered to a subject is from about 1 mg to about 40 mg, from about 1 mg to about 10 mg, from about 10 mg to about 20 mg, from about 20 mg to about 20 mg, or from about 20 mg to about 40 mg. In specific embodiments, the daily dose of the antifungal administered to a subject is about 1.5 mg, about 2 mg, about 2.5 mg, about 3 mg, about 4 mg, about 5 mg, about 6 mg, about 9 mg, about 12 mg, about 15 mg, about 18 mg, about 21 mg, or about 24 mg.

In certain embodiments, the topical antifungal formulations disclosed herein result in mycological cure in human subjects when other topical formulations of anti-mycotics (e.g. terbinafine or itraconazole) have failed to successfully treat the infection according to the mycological cure rate. In certain embodiments, the topical antifungal formulations disclosed herein demonstrate a mycological cure rate of greater than 90% in human toes 14 weeks after the initial application of the topical formulation to the infected nail and/or the surrounding skin. In certain embodiments, the topical antifungal formulations disclosed herein result in a higher mycological cure rate(s) than currently available topical antifungal formulations. The preferred topical antifungal formulations of the invention achieve clean nail growth comparable to oral terbinafine. The preferred topical antifungal formulations of the invention achieve a higher mycological cure rate than oral terbinafine. The preferred topical antifungal formulations of the invention achieve rates of treatment as effective as oral terbinafine.

In certain embodiments, the topical antifungal formulations disclosed herein are used to deliver antifungal non-invasively and predominately to the site of infection via topical administration. The topical antifungal formulations disclosed herein may be administered in place of oral antimycotics, or they may be administered in combination with oral antimycotics. The antifungal formulations disclosed herein should result in a relatively high concentration of the antinfungal in the nail and/or the nail bed compared with the systemic concentration of the antifungal.

The antifungal formulations disclosed herein may be safer than oral, systemic terbinafine formulations. Because the antifungal formulations of the invention are only applied to the site of the infection, the risk of side-effects associated with e.g., oral terbinafine, is reduced, gastrointestinal effects (e.g., feelings of fullness, loss of appetite, dyspepsia, nausea, abdominal pain, diarrhea), skin reactions (e.g., rash, urticaria), musculoskeletal reactions (arthralgia or myalgia) or malaise or tiredness. Other risks reduced by the antifungal formulations disclosed herein include elevated liver enzymes and/or liver failure.

In one embodiment, the invention encompasses a method for preventing onychomycosis, particularly recurrence of onychomycosis, comprising topically administering to a subject a pharmaceutical formulation comprising a therapeutically effective amount of an antifungal described herein, e.g., terbinafine, a lipid, and a surfactant. The antifungal formulations disclosed herein may result in a low rate of recurrence of onychomycosis in a patient. More specifically, the antifungal formulations disclosed herein may have a lower rate of recurrence of onychomycosis than currently available treatments (e.g., Lamisil™ Cream, Lamisil™ Lotion, Lamisil™ Gel or oral Lamisil) after 2 weeks, 6 weeks, 12 weeks, 24 weeks and 48 weeks after last administration.

4. DETAILED DESCRIPTION OF THE INVENTION

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "alkyl" refers to a linear or branched saturated monovalent hydrocarbon radical, wherein the alkyl may optionally be substituted with one or more substituents Q as described herein. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or a branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may also be optionally substituted with one or more substituents Q as described herein.

The term "heteroaryl" refers to a monocyclic aromatic group and/or multicyclic aromatic group that contain at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. The heteroaryl may be attached to the main structure at any heteroatom or carbon atom which results in the creation of a stable compound. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. In certain embodiments, heteroaryl may also be optionally substituted with one or more substituents Q as described herein.

The term "alkenoyl" as used herein refers to —C(O)-alkenyl. The term "alkenyl" refers to a linear or branched monovalent hydrocarbon radical, which contains one or more, in one embodiment, one to five, carbon-carbon double bonds. The alkenyl may be optionally substituted with one or more substituents Q as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 30 ($C_{2-30}$), 2 to 24 ($C_{2-24}$), 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 30 ($C_{3-30}$), 3 to 24 ($C_{3-24}$), 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenoyl is mono-alkenoyl, which contains one carbon-carbon double bond. In certain embodiments, the alkenoyl is di-alkenoyl, which contains two carbon-carbon double bonds. In certain embodiments, the alkenoyl is poly-alkenoyl, which contains more than two carbon-carbon double bonds.

The term "heterocyclyl" or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, acridinyl, azepinyl, benzimidazolyl, benzindolyl, benzoisoxazolyl, benzisoxazinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thienyl, triazinyl, triazolyl, and 1,3,5-trithianyl. In certain embodiments, heterocyclic may also be optionally substituted with one or more substituents Q as described herein.

The term "halogen", "halide" or "halo" refers to fluorine, chlorine, bromine, and/or iodine.

The term "optionally substituted" is intended to mean that a group, including alkyl, alkenyl, alkynyl, cycloalkyl, aryl, aralkyl, heteroaryl, and heterocyclyl, may be substituted with one or more substituents Q, in one embodiment, one, two, three or four substituents Q, where each Q is independently selected from the group consisting of cyano, halo, oxo, nitro, $C_{1-6}$ alkyl, halo-$C_{1-6}$ alkyl, $C_{2-6}$ alkenyl, $C_{2-6}$ alkynyl, $C_{3-7}$ cycloalkyl, $C_{6-14}$ aryl, $C_{7-14}$ aralkyl, heteroaryl, heterocyclyl, —C(O)$R^e$, —C(O)O$R^e$, —C(O)NR$^f$R$^g$, —C(NR$^e$)NR$^f$R$^g$, —O$R^e$, —OC(O)$R^e$, —OC(O)O$R^e$, —OC(O)NR$^f$R$^g$, —OC(=NR$^e$)NR$^f$R$^g$, —OS(O)$R^e$, —OS(O)$_2$$R^e$, —OS(O)NR$^f$R$^g$, —OS(O)$_2$NR$^f$R$^g$, —NR$^f$R$^g$, —NR$^e$C(O)$R^f$, —NR$^e$C(O)O$R^f$, —NR$^e$C(O)NR$^f$R$^g$, —NR$^e$C(=NR$^h$)NR$^f$R$^g$, —NR$^e$S(O)$R^f$, —NR$^e$S(O)$_2$$R^f$, —NR$^e$S(O)NR$^f$R$^g$, —NR$^e$S(O)$_2$NR$^f$R$^g$, —S$R^e$, —S(O)$R^e$, —S(O)$_2$$R^e$, and —S(O)$_2$NR$^f$R$^g$, wherein each $R^e$, $R^f$, $R^g$, and $R^h$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-14}$ aralkyl, heteroaryl, or heterocyclyl; or $R^f$ and $R^g$ together with the N atom to which they are attached form heterocyclyl.

The terms "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

The antifungal formulations provided herein comprise an antifungal, a lipid, preferably a phospholipid, a surfactant, preferably a nonionic surfactant, and an aqueous solution, having a pH ranging from 3.5 to 9.0, preferably from 4 to 7.5. The antifungal formulations provided herein may contain an antifungal, or a pharmaceutically acceptable solvate, hydrate, or salt of the antifungal. The antifungal formulations may optionally contain buffers, antioxidants, preservatives, microbicides, antimicrobials, and/or thickeners. In certain embodiments, a certain portion of the antifungal in the pharmaceutical composition is in salt form.

While not to be limited by any mechanism of action, the terbinafine formulations of the invention preferably form vesicles or other extended surface aggregates (ESAs), wherein the vesicular preparations have improved permeation capability through the semi-permeable barriers, such as skin and/or nails. The vesicles or extended surface aggregates of the present invention are comprised of terbinafine, a lipid, and one or more membrane destabilizing agents, such as surfactants.

4.1. Antifungals

The pharmaceutical compositions disclosed herein comprise one or more antifungals. Antifungals include but are not limited to terbinafine, terbinafine derivatives and analogs, allylamines or structurally related analogs, triazoles and/or imidazoles, liranaftate and tolnaftate, grisefulvin, and mixtures and/or combinations thereof.

4.1.1. Terbinafine

Terbinafine belongs to the class of allylamine anti-mycotics. The structure of terbinafine is shown in formula I below:

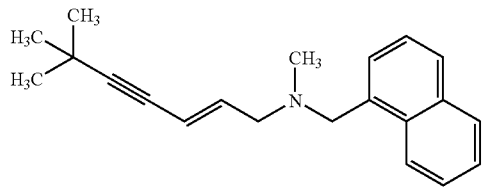

I

Terbinafine may be used as the antifungal in the formulations disclosed herein in its free base or salt form. In a specific embodiment, terbinafine is used as a hydrochloride (HCl) salt, herein referred to as terbinafine-HCl. The term "terbinafine" as used herein includes the free base form of this compound as well as therapeutically acceptable acid addition salts thereof. Suitable salt forms include chloride, bromide, iodide, acetate, and fumarate, but in principle any pharmaceutically acceptable anion can be used.

The pharmaceutical formulations containing terbinafine provided herein allow for the topical administration of terbinafine, and comprise a therapeutically effective amount of terbinafine and at least one lipid and at least one surfactant, wherein the formulation comprises 0.25-25.0% terbinafine in terms of dry "total lipid" weight being defined as the sum total of dry weights of all included lipids, surfactants, lipophilic excipients and the drug. The pharmaceutical formulations containing terbinafine provided herein may also comprise 0.25 to 30% terbinafine by weight or about 0.5% to about 10% by weight. In specific embodiments, the pharmaceutical formulations containing terbinafine provided herein may comprise from about 0.25% to about 0.5%, about 0.5% to about 1.0%, about 1.0% to about 1.5%, about 1.5% to about 2.0%, about 2.0% to about 2.5%, about 2.5% to about 3.0%, about 3.0%, to about 4.0%, about 5.0% to about 6.0%, about 6.0% to about 7.0%, about 7.0% to about 8.0%, about 8.0% to about 9.0%, about 9.0% to about 10% terbinafine, from about 10% to about 12%, about 12% to about 14%, about 14% to about 16%, about 16% to about 18%, about 18% to about 20%, about 22% to about 24%, about 26%, to about 28%, about 28% to about 30% terbinafine by weight. In an embodiment, the pharmaceutical formulations containing terbinafine comprise about 1.5% terbinafine by weight.

The pharmaceutical formulations containing terbinafine provided herein contain terbinafine in an amount ranging from about 0.25 mg/g to about 200 mg/g. In certain embodiments, the amount of terbinafine may range from about 0.25 mg/g to about 200 mg/g, from about 0.5 mg/g to about 175 mg/g, from about 0.5 mg/g to about 150 mg/g, from about 0.5 mg/g to about 100 mg/g, from about 0.5 mg/g to about 75 mg/g, from about 0.5 mg/g to about 50 mg/g, from about 0.5 mg/g to about 25 mg/g, from about 0.5 mg/g to about 20 mg/g, from about 0.5 mg/g to about 10 mg/g, from about 0.5 mg/g to about 5 mg/g, from about 0.5 mg/g to about 4 mg/g, from about 0.5 mg/g to about 3 mg/g, from about 0.5 mg/g to about 2 mg/g, and from about 0.5 mg/g to about 1.5 mg/g.

The pharmaceutical formulations containing terbinafine provided herein also typically comprise a polar liquid medium. The terbinafine formulations of the invention is typically administered in an aqueous medium. The terbinafine formulations of the present invention may be in the form of a solution, suspension, gel, fluid gel, emulsion, emulsion gel, cream, lotion, ointment, spray, film forming solution, lacquer or a patch soaked with the formulation.

4.1.2. Terbinafine Derivatives and Analogs

The antifungal of the pharmaceutical formulations provided herein can also comprise allyamines, including terbinafine derivatives and analogs. In some embodiments, the terbinafine derivative or analog is a compound of formula IA,

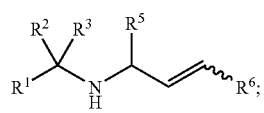

IA wherein (a) $R^1$ represents a group of formula

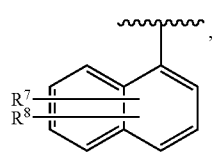

IIa

-continued

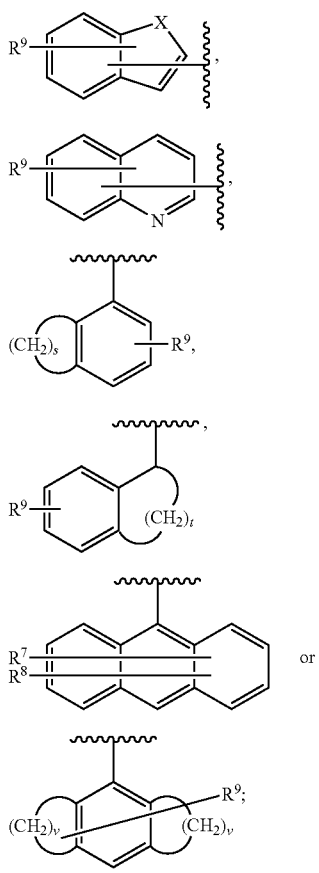

and $R^2$ represents hydrogen or lower alkyl, or $R^1$ and $R^2$ together represent a group of formula

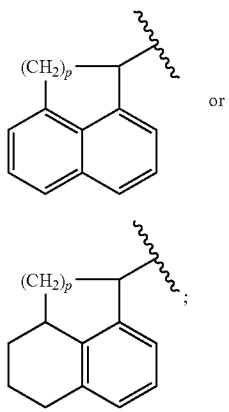

whereby in the formulae IIa to IIi, $R^7$ and $R^8$ represent, independently, hydrogen, halogen, trifluoromethyl, hydroxy, nitro, lower alkyl, lower alkoxy, or —C(=O)—$R^{15}$, wherein $R^{15}$ represents H, hydroxyl, lower alkyl, alkoxy (so that $R^{15}$ together with the carbonyl group is an ester), or amino (so that $R^{15}$ together with the carbonyl group is carbamoyl);

$R^9$ represents hydrogen, halogen, hydroxy, lower alkyl or lower alkoxy,

X represents oxygen, sulphur, imino, lower alkyl imino or a radical of formula —$(CH_2)_r$—, p is 1, 2 or 3,
r is 1, 2 or 3,
s is 3, 4 or 5,
t is 2, 3 or 4, and
v is 3, 4, 5 or 6;

$R^3$ and $R^5$ represent, independently, hydrogen or lower alkyl, and $R^4$ represents $C_{1-6}$ alkyl or $C_{3-8}$ cycloalkyl-$(C_{1-6})$-alkyl; and $R^6$ represents a group of formula wherein $R^{11}$ represents hydrogen, $(C_{1-6})$ alkyl, optionally α-hydroxy substituted alkyl; alkenyl, alkynyl, cycloalkyl, cycloalkylalkyl, phenyl, phenalkyl or thienyl, $R^{12}$, $R^{13}$, and $R^{14}$ represent, independently, hydrogen or lower alkyl, and represents a $C_{5-8}$ cycloalkylidene radical optionally containing a double bond; or (b) $R^1$ represents a group of formula IIa to IIg as defined under (a), $R^2$ represents hydrogen or lower alkyl, $R^3$ and $R^4$ together form a group —$(CH_2)_u$—, wherein u is an integer of 1 to 8, and $R^5$ and $R^6$ have the meanings given under (a).

Any lower alkyl or lower alkoxy radical has preferably 1 to 4 carbon atoms, especially 2 or 1 carbon atoms. Unless otherwise stated alkyl moieties preferably have 1 to 12 carbon atoms especially 2 to 8 carbon atoms, particularly 2 to 6 carbon atoms and most preferably 3 to 5 carbon atoms and if bridging 1 to 4 particularly 1 or 2 carbon atoms. Any alkenyl or alkynyl radical has preferably 3 to 6 carbon atoms, especially 3 to 4 carbon atoms, e.g. allyl, propenyl or propynyl. Such alkyl, alkoxy, alkenyl and alkinyl groups can be straight-chain or branched. A preferred cycloalkylidene radical is cyclohexylidene. The term cycloalkyl is to be understood as including polycyclo groups such as bornyl or adamantyl but is preferably cyclohexyl or cyclopentyl.

In specific embodiments, $R^7$ and $R^8$ are identical and are both hydrogen. In specific embodiments, $R^9$ is hydrogen or halogen. In specific embodiments, IIb and IIc the bond to the carbon atom to which $R^2$ and $R^3$ are attached is attached meta to X and para to the ring nitrogen, respectively. In specific embodiments, X is sulphur, imino or lower alkylamino. $R^1$ is preferably a radical of formula IIb, IIc or IId, or especially IIa. $R^2$ is preferably hydrogen. $R^3$ is preferably hydrogen and $R^4$ is, in specific embodiments, alkyl. In specific embodiments, $R^5$ is hydrogen.

In specific embodiments, the values of p, r, s, t, u and v are chosen to produce a seven- preferably a five- or six-membered ring.

The double bond between $R^6$ and the nitrogen atom preferably has the trans-configuration. Halogen stands for fluorine, chlorine or bromine, preferably chlorine or bromine.

In certain embodiments, the compound of formula IA is as defined in U.S. Pat. No. 4,755,534, the disclosure of which is hereby incorporated by reference in its entirety.

In a specific embodiment the compound of formula IA is:

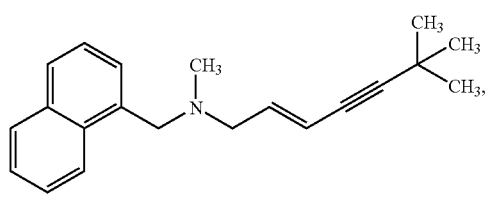

which is also known as terbinafine.

In a specific embodiment, the compound of formula IA is:

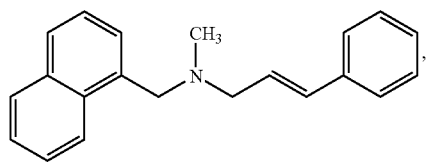

which is also known as naftifine.

In a specific embodiment, the compound of formula IA is:

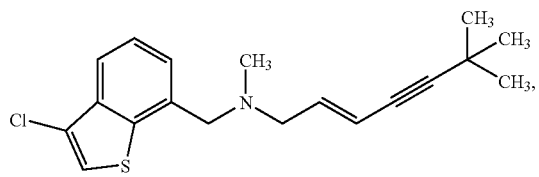

which is described in Ryder et al. 1992, Current Topics in Medical Mycology. Vol. 4, pp. 158-188.

In certain embodiments, analogs of terbinafine are described by U.S. Patent Publication No. 2007/0244336 the disclosure of which is hereby incorporated by reference in its entirety. In certain embodiments, salts of terbinafine are described by U.S. Patent Publication No. 2006/0004230, the disclosure of which is hereby incorporated by reference in its entirety. In certain embodiments, antifungal allylamine derivatives are described by U.S. Patent Publication No. 2005/0032904, the disclosure of which is hereby incorporated by reference in its entirety.

4.1.2. Allylamines or Structurally Related Analogs

Allyamines or structurally related analog that are suitable for use in the topical antifungal formulations provided herein include, but are limited to, amorolfine, butenafine, and naftifine.

In one embodiment, the allyamine or structurally related analog in the topical antifungal formulations provided herein is amorolfine having the structure of:

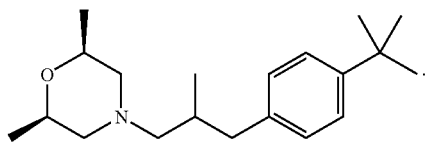

In another embodiment, the allyamine or structurally related analog in the topical antifungal formulations provided herein is butenafine having the structure of:

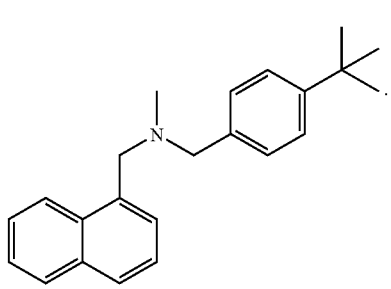

In yet another embodiment, the allyamine or structurally related analog in the topical antifungal formulations provided herein is naftifine having the structure of:

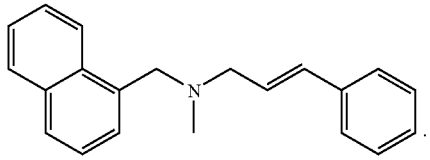

The allyamine or structurally related analog may be used in the formulations provided herein in its free base, or its pharmaceutically acceptable solvate, hydrate, or salt form. In a specific embodiment, the allyamine or structurally related analog is used as a hydrochloride (HCl) salt. The term "allyamine or structurally related analog" as used herein includes the free base form of the compound as well as pharmaceutically acceptable solvate, hydrate, or salt form. Suitable salt forms include, but are not limited to chloride, bromide, iodide, acetate, and fumarate.

The pharmaceutical formulations provided herein allow for the topical administration of the allyamine or structurally related analog, and comprise a therapeutically effective amount of the allyamine or structurally related analog and at least one lipid and at least one surfactant, wherein the formulation comprises 0.25-25.0% of the allyamine or structurally related analog in terms of dry "total lipid" weight being defined as the sum total of dry weights of all included lipids, surfactants, lipophilic excipients, and the allyamine. The formulations provided herein may also comprise 0.25 to 30% by weight or about 0.5% to about 10% by weight of the allyamine or structurally related analog. In specific embodiments, the topical formulations may comprise from about 0.25% to about 0.5%, from about 0.5% to about 1%, from about 1% to about 1.5%, from about 1.5% to about 2%, from about 2% to about 2.5%, from about 2.5% to about 3%, from about 3% to about 4%, from about 4% to about 5%, from about 5% to about 6%, from about 6% to about 7%, from about 7% to about 8%, from about 8% to about 9%, from about 9% to about 10%, from about 10% to about 12%, from about 12% to about 14%, from about 14% to about 16%, from about 16% to about 18%, from about 18% to about 20%, from about 22% to about 24%, from about 26% to about 28%, or from about 28% to about 30% by weight of the allyamine or structurally related analog.

The pharmaceutical formulations provided herein contain the allyamine or structurally related analog in an amount ranging from about 0.25 mg/g to about 200 mg/g. In certain embodiments, the amount of the allyamine or structurally related analog in the pharmaceutical formulations may range from about 0.25 mg/g to about 200 mg/g, from about 0.5 mg/g to about 175 mg/g, from about 0.5 mg/g to about 150 mg/g, from about 0.5 mg/g to about 100 mg/g, from about 0.5 mg/g to about 75 mg/g, from about 0.5 mg/g to about 50 mg/g, from about 0.5 mg/g to about 25 mg/g, from about 0.5 mg/g to about 20 mg/g, from about 0.5 mg/g to about 10 mg/g, from about 0.5 mg/g to about 5 mg/g, from about 0.5 mg/g to about 4 mg/g, from about 0.5 mg/g to about 3 mg/g, from about 0.5 mg/g to about 2 mg/g, or from about 0.5 mg/g to about 1.5 mg/g.

In certain embodiments, the topical formulations provided herein also comprise a polar liquid medium. In certain embodiments, the topical formulations provided herein are administered in an aqueous medium. The topical formulations provided herein may be in the form of a solution, suspension, gel, fluid gel, emulsion, emulsion gel, cream, lotion, ointment, spray, film forming solution, lacquer or a patch soaked with the formulation.

4.1.3. Triazoles and/or Imidazoles

In certain embodiments, the antifungal formulations disclosed herein include triazoles and. or imidazoles, e.g., having the structure of Formula I:

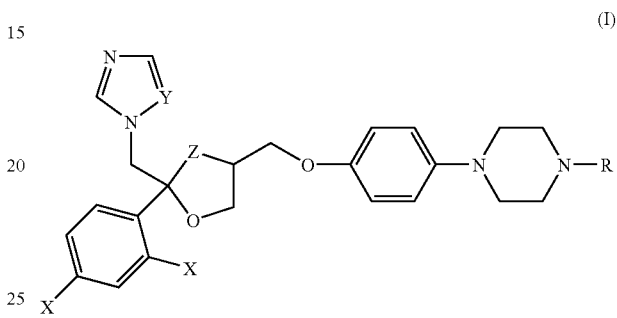

(I)

or a single enantiomer, a mixture of enantiomers, or a mixture of diastereomers thereof; or a pharmaceutically acceptable solvate, hydrate, or salt thereof; wherein:

R is $C_{1-12}$ alkyl, $C_{1-12}$ acyl, or heteroaryl-$C_{6-14}$ aryl;

X is halo;

Y is N or CH; and

Z is $CH_2$ or O.

The groups, R, X, Y, and Z in Formula I are further defined herein. All combinations of the embodiments provided herein for such groups are within the scope of this disclosure.

In certain embodiments, R is $C_{1-12}$ alkyl. In certain embodiments, R is isopropyl. In certain embodiments, R is $C_{1-12}$ acyl. In certain embodiments, R is acetyl. In certain embodiments, R is heteroaryl-$C_{6-14}$ aryl. In certain embodiments, R is 1-sec-butyl-1H-1,2,4-triazol-5(4H)-one-4-yl, 1-(2-hydroxypentan-3-yl)-1H-1,2,4-triazol-5(4H)-one-4-yl, or 1-((2S,3R)-2-hydroxypentan-3-yl)-1H-1,2,4-triazol-5(4H)-one-4-yl.

In certain embodiments, each X is independently fluoro or chloro. In certain embodiments, X is fluoro. In certain embodiments, X is chloro.

In certain embodiments, Y is N. In certain embodiments, Y is CH.

In certain embodiments, Z is $CH_2$. In certain embodiments, Z is O.

In one embodiment, provided herein is a compound of Formula I, wherein R is isopropyl, acetyl, 1-sec-butyl-1H-1,2,4-triazol-5(4H)-one-4-yl, 1-(2-hydroxypentan-3-yl)-1H-1,2,4-triazol-5(4H)-one-4-yl, or 1-((2S,3R)-2-hydroxypentan-3-yl)-1H-1,2,4-triazol-5(4H)-one-4-yl; each X is independently fluoro or chloro; Y is N or CH; and Z is $CH_2$ or O.

In one embodiment, the compound of Formula I is itraconazole having the structure of:

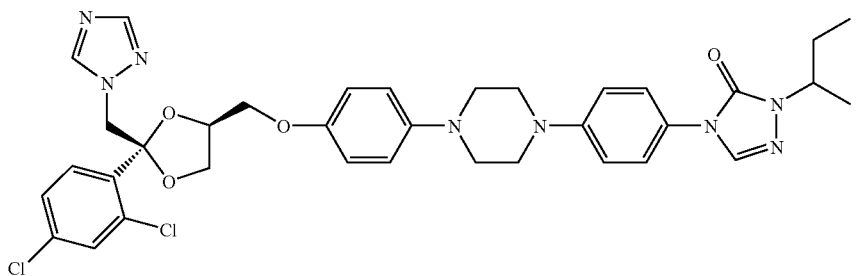

or a single enantiomer or a mixture of diastereomers thereof or a pharmaceutically acceptable solvate, hydrate, or salt thereof.

In another embodiment, the compound of Formula I is ketoconazole having the structure:

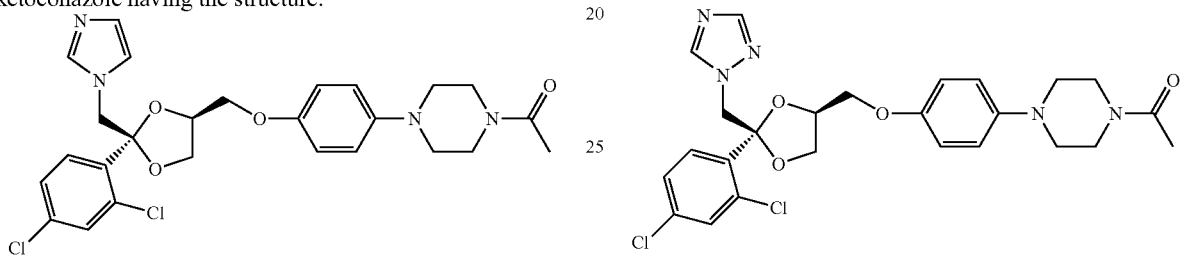

or a pharmaceutically acceptable solvate, hydrate, or salt thereof.

In yet another embodiment, the compound of Formula I is posaconazole having the structure of:

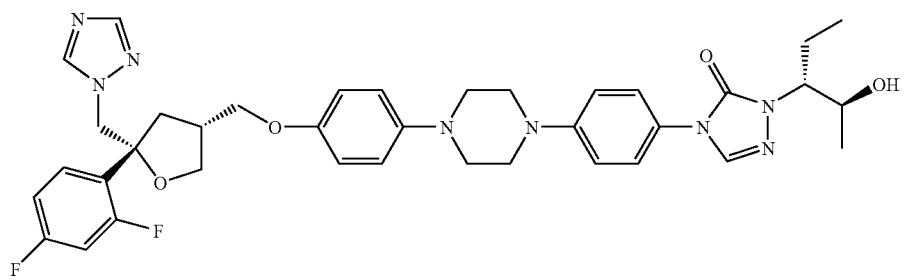

or a pharmaceutically acceptable solvate, hydrate, or salt thereof.

In yet another embodiment, the compound of Formula I is terconazole having the structure of:

or a pharmaceutically acceptable solvate, hydrate, or salt thereof.

In yet another embodiment, the compound of Formula I is SCH-50002 having the structure of:

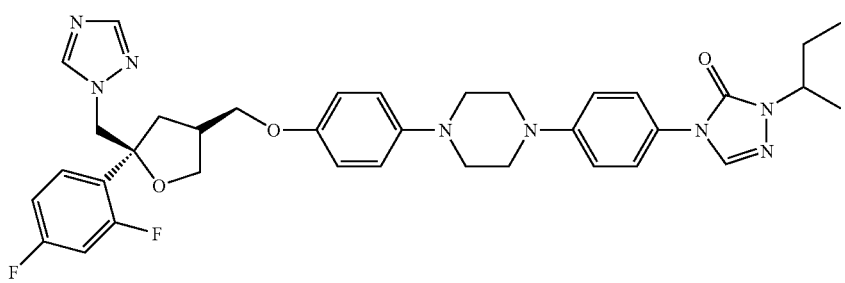

or a single enantiomer or a mixture of diastereomers thereof; or a pharmaceutically acceptable solvate, hydrate, or salt thereof.

In still another embodiment, the compound of Formula I is saperconazole having the structure of:

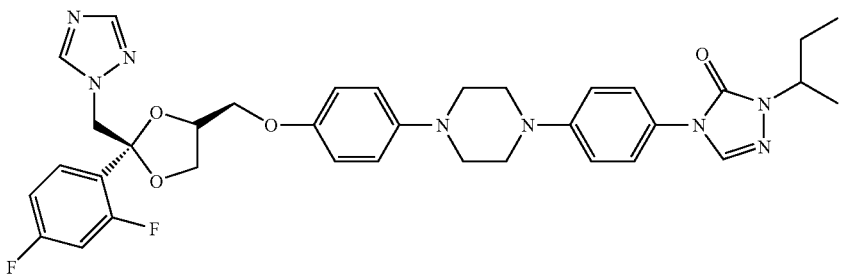

or a single enantiomer or a mixture of diastereomers thereof; or a pharmaceutically acceptable solvate, hydrate, or salt thereof.

In still another embodiment, the triazole and/or imidazole antifungal is fluconazole, having the structure of:

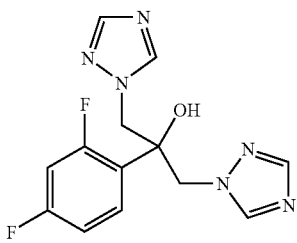

or a single enantiomer or a mixture of diastereomers thereof; or a pharmaceutically acceptable solvate, hydrate, or salt thereof.

In still another embodiment, the triazole and/or imidazole antifungal is voriconazole, having the structure of:

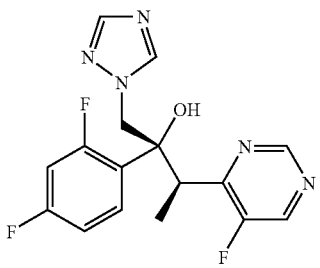

or a single enantiomer or a mixture of diastereomers thereof; or a pharmaceutically acceptable solvate, hydrate, or salt thereof.

Triazole and/or imidazole antifungals as provided herein may be used in the formulations provided herein as a single enantiomer, a mixture of enantiomers, or a mixture of diastereomers thereof; or a pharmaceutically acceptable solvate, hydrate, or salt thereof. In a specific embodiment, triazole and/or imidazole antifungals are used in their free base forms.

The term "a triazole and/or imidazole antifungal" as used herein includes the free base form of the compound, including single enantiomers, mixtures of enantiomers, and mixtures of diastereomers of the compound; as well as pharmaceutically acceptable solvates, hydrates, and salts of the compound, including its single enantiomers, mixtures of enantiomers, and mixtures of diastereomers.

The pharmaceutical formulations provided herein allow for the topical administration of triazole and/or imidazole antifungals, e.g., itraconazole, ketoconazole, posaconazole, saperconazole, SCH-50002, terconazole, fulconazole, or voriconazole, and comprise a therapeutically effective amount of a triazole or imidazole antifungal provided herein, and at least one lipid and at least one surfactant, wherein the formulation comprises 0.25-25% of the antifungal in terms of dry "total lipid" weight being defined as the sum total of dry weights of all included lipids, surfactants, lipophilic excipients, and the antifungal. The formulations provided herein may also comprise 0.25 to 30% by weight or about 0.5% to about 10% by weight of the antifungal. In specific embodiments, the topical antifungal formulations may comprise from about 0.25% to about 0.5%, from about 0.5% to about 1%, from about 1% to about 1.5%, from about 1.5% to about 2%, from about 2% to about 2.5%, from about 2.5% to about 3%, from about 3% to about 4%, from about 4% to about 5%, from about 5% to about 6%, from about 6% to about 7%, from about 7% to about 8%, from about 8% to about 9%, from about 9% to about 10%, from about 10% to about 12%, from about 12% to about 14%, from about 14% to about 16%, from about 16% to about 18%, from about 18% to about 20%, from about 22% to about 24%, from about 26% to about 28%, or from about 28% to about 30% by weight of the triazole and/or imidazole antifungal.

The pharmaceutical formulations provided herein contain the triazole and/or imidazole antifungal in an amount ranging from about 0.25 mg/g to about 200 mg/g. In certain embodiments, the amount of the triazole or imidazole antifungal in the pharmaceutical formulations may range from about 0.25 mg/g to about 200 mg/g, from about 0.5 mg/g to about 175 mg/g, from about 0.5 mg/g to about 150 mg/g, from about 0.5 mg/g to about 100 mg/g, from about 0.5 mg/g to about 75 mg/g, from about 0.5 mg/g to about 50 mg/g, from about 0.5 mg/g to about 25 mg/g, from about 0.5 mg/g to about 20 mg/g, from about 0.5 mg/g to about 10 mg/g, from about 0.5 mg/g to about 5 mg/g, from about 0.5 mg/g to about 4 mg/g, from about 0.5 mg/g to about 3 mg/g, from about 0.5 mg/g to about 2 mg/g, or from about 0.5 mg/g to about 1.5 mg/g.

In certain embodiments, the antifungal formulations provided herein also comprise a polar liquid medium. In certain embodiments, the antifungal formulations provided herein are administered in an aqueous medium. The antifungal formulations provided herein may be in the form of a solution, suspension, gel, fluid gel, emulsion, emulsion gel, cream, lotion, ointment, spray, film forming solution, lacquer or a patch soaked with the formulation.

The antifungals provided herein are intended to encompass all possible stereoisomers, including enantiomers and diastereomers and mixtures thereof, unless a particular stereochemistry is specified. Where an antifungals provided herein contains an alkenyl or alkenylene group, the antifungal may exist as a cis (Z) or trans (E) isomer or as a mixture of geometric cis/trans (or Z/E) isomers. Where structural isomers are interconvertible via a low energy barrier, the antifungal may exist as a single tautomer or a mixture of tautomers. This can take the form of proton tautomerism in the antifungal that contains, for example, an imino, keto, or oxime group; or so-called valence tautomerism in the antifungal that contain an aromatic moiety. It is understood that a single antifungal may exhibit more than one type of isomerism.

The antifungals provided herein may be enantiomerically pure, such as a single enantiomer or a single diastereomer, or may be stereoisomeric mixtures, such as a mixture of enantiomers, a racemic mixture, or a diastereomeric mixture. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the antifungals provided herein contain an acidic or basic moiety, they may also be provided as pharmaceutically acceptable salts (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts include, but are not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

4.1.4. Liranaftate and Tolnaftate

Liranaftate is an antifungal having the structure of:

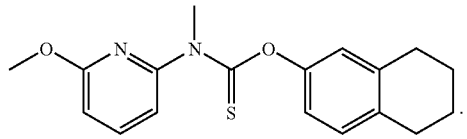

Tolnaftate is an antifungal having the structure of:

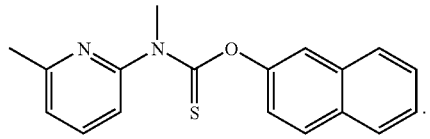

Liranaftate or tolnaftate may be used in the formulations provided herein in its free form, or its pharmaceutically acceptable solvate, hydrate, or salt form. In a specific embodiment, liranaftate or tolnaftate is used in its free form. The term "liranaftate" as used herein includes the free form of the compound as well as pharmaceutically acceptable solvate, hydrate, or salt form. The term "tolnaftate" as used herein includes the free form of the compound as well as pharmaceutically acceptable solvate, hydrate, or salt form.

The pharmaceutical formulations provided herein allow for the topical administration of liranaftate or tolnaftate, and comprise a therapeutically effective amount of liranaftate or tolnaftate and at least one lipid and at least one surfactant, wherein the formulation comprises 0.25-25% liranaftate or tolnaftate in terms of dry "total lipid" weight being defined as the sum total of dry weights of all included lipids, surfactants, lipophilic excipients, and liranaftate or tolnaftate. The formulations provided herein may also comprise 0.25 to 30% by weight or about 0.5% to about 10% by weight of liranaftate or tolnaftate. In specific embodiments, the topical formulations may comprise from about 0.25% to about 0.5%, from about 0.5% to about 1%, from about 1% to about 1.5%, from about 1.5% to about 2%, from about 2% to about 2.5%, from about 2.5% to about 3%, from about 3% to about 4%, from about 4% to about 5%, from about 5% to about 6%, from about 6% to about 7%, from about 7% to about 8%, from about 8% to about 9%, from about 9% to about 10%, from about 10% to about 12%, from about 12% to about 14%, from about 14% to about 16%, from about 16% to about 18%, from about 18% to about 20%, from about 22% to about 24%, from about 26% to about 28%, or from about 28% to about 30% by weight of liranaftate or tolnaftate.

The pharmaceutical formulations provided herein contain liranaftate or tolnaftate in an amount ranging from about 0.25 mg/g to about 200 mg/g. In certain embodiments, the amount of liranaftate or tolnaftate in the pharmaceutical formulations may range from about 0.25 mg/g to about 200 mg/g, from about 0.5 mg/g to about 175 mg/g, from about 0.5 mg/g to about 150 mg/g, from about 0.5 mg/g to about 100 mg/g, from about 0.5 mg/g to about 75 mg/g, from about 0.5 mg/g to about 50 mg/g, from about 0.5 mg/g to about 25 mg/g, from about 0.5 mg/g to about 20 mg/g, from about 0.5 mg/g to about 10 mg/g, from about 0.5 mg/g to about 5 mg/g, from about 0.5 mg/g to about 4 mg/g, from about 0.5 mg/g to about 3 mg/g, from about 0.5 mg/g to about 2 mg/g, or from about 0.5 mg/g to about 1.5 mg/g.

In certain embodiments, the topical formulations provided herein also comprise a polar liquid medium. In certain embodiments, the topical formulations provided herein are administered in an aqueous medium. The topical formulations provided herein may be in the form of a solution, suspension, gel, fluid gel, emulsion, emulsion gel, cream, lotion, ointment, spray, film forming solution, lacquer or a patch soaked with the formulation.

4.1.5. Grisefulvin

Griseofulvin is an antifungal having the structure of:

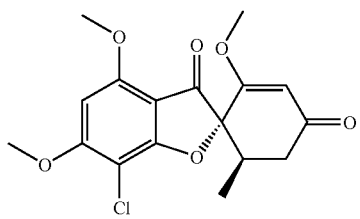

Griseofulvin may be used in the formulations provided herein in its free form, or its pharmaceutically acceptable solvate, hydrate, or salt form. In a specific embodiment, griseofulvin is used in its free form. The term "griseofulvin" as used herein includes the free form of the compound as well as pharmaceutically acceptable solvate, hydrate, or salt form.

The pharmaceutical formulations provided herein allow for the topical administration of griseofulvin, and comprise a therapeutically effective amount of griseofulvin and at least one lipid and at least one surfactant, wherein the formulation comprises 0.25-25% griseofulvin in terms of dry "total lipid" weight being defined as the sum total of dry weights of all included lipids, surfactants, lipophilic excipients, and griseofulvin. The formulations provided herein may also comprise 0.25 to 30% by weight or about 0.5% to about 10% by weight of griseofulvin. In specific embodiments, the topical griseofulvin formulations may comprise from about 0.25% to about 0.5%, from about 0.5% to about 1%, from about 1% to about 1.5%, from about 1.5% to about 2%, from about 2% to about 2.5%, from about 2.5% to about 3%, from about 3% to about 4%, from about 4% to about 5%, from about 5% to about 6%, from about 6% to about 7%, from about 7% to about 8%, from about 8% to about 9%, from about 9% to about 10%, from about 10% to about 12%, from about 12% to about 14%, from about 14% to about 16%, from about 16% to about 18%, from about 18% to about 20%, from about 22% to about 24%, from about 26% to about 28%, or from about 28% to about 30% by weight of griseofulvin.

The pharmaceutical formulations provided herein contain griseofulvin in an amount ranging from about 0.25 mg/g to about 200 mg/g. In certain embodiments, the amount of griseofulvin in the pharmaceutical formulations may range from about 0.25 mg/g to about 200 mg/g, from about 0.5 mg/g to about 175 mg/g, from about 0.5 mg/g to about 150 mg/g, from about 0.5 mg/g to about 100 mg/g, from about 0.5 mg/g to about 75 mg/g, from about 0.5 mg/g to about 50 mg/g, from about 0.5 mg/g to about 25 mg/g, from about 0.5 mg/g to about 20 mg/g, from about 0.5 mg/g to about 10 mg/g, from about 0.5 mg/g to about 5 mg/g, from about 0.5 mg/g to about 4 mg/g, from about 0.5 mg/g to about 3 mg/g, from about 0.5 mg/g to about 2 mg/g, or from about 0.5 mg/g to about 1.5 mg/g.

In certain embodiments, the griseofulvin formulations provided herein also comprise a polar liquid medium. In certain embodiments, the griseofulvin formulations provided herein are administered in an aqueous medium. The griseofulvin formulations provided herein may be in the form of a solution, suspension, gel, fluid gel, emulsion, emulsion gel, cream, lotion, ointment, spray, film forming solution, lacquer or a patch soaked with the formulation.

4.2. Lipid

In the sense of this invention, a "lipid" is any substance, which has properties like or similar to those of a fat. As a rule, it has an extended apolar group (the "chain", X) and generally also a water-soluble, polar hydrophilic part, the "head" group (Y) and has the basic formula II.

$$X-Y_n \qquad (II)$$

wherein n is equal to or larger than zero. Lipids with n=0 are referred to as apolar lipids and lipids with n≧1 are referred to as polar lipids. In this sense, all amphiphilic substances, including, but not limited to glycerides, glycerophospholipids, glycerophosphinolipids, glycerophosphonolipids, sulfolipids, sphingolipids, isoprenoid lipids, steroids or sterols and carbohydrate-containing lipids can generally be referred to as lipids, and are included as such in this invention. A list of relevant lipids and lipid related definitions is provided in EP 0 475 160 A1 (see, e.g. p. 4, 1. 8 to p. 6, 1. 3) and U.S. Pat. No. 6,165,500 (see, e.g., col. 6, 1. 10 to col. 7, 1. 58), which are herewith incorporated by reference.

A phospholipid is, for example, a compound of formula III:

$$R^1-CH_2-CHR^2-CR^3H-O-PHO_2-O-R^4 \qquad (III)$$

wherein $R^1$ and $R^2$ cannot both be hydrogen, OH or a $C_1$-$C_3$ alkyl group, and typically are independently, an aliphatic chain, most often derived from a fatty acid or a fatty alcohol. $R^3$ generally is a hydrogen. The OH-group of the phosphate is a hydroxyl radical or hydroxyl anion (i.e., hydroxide) form, dependent on degree of the group ionization. Furthermore, $R^4$ may be a proton or a short-chain alkyl group, substituted by a tri-short-chain alkylammonium group, such as a trimethylammonium group, or an amino-substituted short-chain alkyl group, such as 2-trimethylammonium ethyl group (cholinyl) or 2-dimethylammonium short alkyl group.

A sphingophospholipid is, for example, a compound of formula IIIB:

$$R^1\text{-Sphingosine-O}-PHO_2-O-R^4 \qquad (IIIB)$$

wherein $R^1$ is a fatty-acid attached via an amide bond to the nitrogen of the sphingosine and $R^4$ has the meanings given under formula III.

A lipid preferably is a substance of formulae III or IIIB, wherein $R^1$ and/or $R^2$ are acyl or alkyl, n-hydroxyacyl or n-hydroxyalkyl, but may also be branched, with one or more methyl groups attached at almost any point of the chain; usually, the methyl group is near the end of the chain (iso or anteiso). The radicals $R^1$ and $R^2$ may moreover either be saturated or unsaturated (mono-, di- or poly-unsaturated). $R^3$ is hydrogen and $R^4$ is 2-trimethylammonium ethyl (the latter corresponds to the phosphatidyl choline head group), 2-dimethylammonium ethyl, 2-methylammonium ethyl or 2-aminoethyl (corresponding to the phosphatidyl ethanolamine head group). $R^4$ may also be a proton (giving phosphatidic acid), a serine (giving phosphatidylserine), a glycerol (giving phosphatidylglycerol), an inositol (giving phosphatidylinositol), or an alkylamine group (giving phosphatidylethanolamine in case of an ethylamine), if one chooses to use a naturally occurring glycerophospholipid. Otherwise, any other sufficiently polar phosphate ester, such that will form a lipid bilayer, may be considered as well for making the formulations of the invention.

Table 1 lists preferred phospholipids in accordance with the invention.

The fatty acid- or fatty alcohol-derived chain of a lipid is typically selected amongst the basic aliphatic chain types given in the following tables:

TABLE 2

The (most) preferred basic, straight, saturated fatty chain residues

| Shorthand designation | Systematic name | Trivial name |
|---|---|---|
| 12:0 | Dodecanoic | Lauric |
| 13:0 | Tridecanoic | |
| 14:0 | Tetradecanoic | Myristic |

TABLE 1

Preferred (phospho)lipids for use in combination with the antifungal

| Name(s) | Fatty chain Length: nr. of double bonds | Phospholipid Type/Charge | | | | |
|---|---|---|---|---|---|---|
| | | Phosphatidylcholine/+ Main lipid, L1 | Sphingomyelin/+ Main lipid, L1 | Phosphatidylglycerol/− Aux. lipid, L2 | Phosphatidylinositol/− Aux. lipid, L2 | Phosphatidic acid/− Aux. lipid, L2 |
| Behen(o)yl | C24 | | | | | |
| Eruca(o)yl | C22 | | | | | |
| | C22:1-13cis | | | | | |
| Arachin(o)yl | C20 | | | | | |
| Gadolen(o)yl | C20:1-11cis | | | | | |
| Arachidon(o)yl | C20:4-5,8,11,14cis | | | | | |
| Ole(o)yl | C18:1-9cis | DOPC | SM-oleyl | DOPG | DOPI | DOPA |
| Stear(o)yl | C18 | | | | | |
| Linol(o)yl | C18:2-9,12cis | (Soy-PC/ | Brain SM | (Soy-PC/ | (Soy-PI/ | (Soy-PA/ |
| Linole(n/o)yl | C18:3-9,12,15cis | Egg-PC) | | Egg-PC) | Liver-PI) | Egg-PA) |
| Palmitole(o)yl | C18:1-9cis | | | | | |
| Palmit(o)yl | C16 | | | | | |
| Myrist(o)yl | C14 | DMPC | SM-myristyl | DMPG | DMPI | |
| Laur(o)yl | C12 | DLPC | SM-lauryl | | | DLPA |
| Capr(o)yl | C10 | | | | | |
| Rel. concentration range L1/L2 (M/M) | | 1/0 | 1/0 | 10/1-1/1 | 10/1-3/1 | 10/1-5/1 |
| "Total Lipid"* concentration range (w-%) | | 0.5-45 | 0.5-45 | 0.5-40 | 0.5-40 | 0.5-40 |

*Total Lipid includes phospholipid(s), surfactant, antifungal, and all lipophilic excipients
The antifungal is incorporated in up to 15 rel. w-% into acidic formulations and up to 10 rel. w-% into neutral pH formulations The preferred basic lipids in context of this invention are uncharged and form stable, well hydrated bilayers; phosphatidylcholines and sphingomyelins are the most prominent representatives of such lipids. Either of those can have chains as listed in the Table 1, the ones forming fluid phase bilayers, in which lipid chains are in disordered state, being preferred.

Different negatively charged, i.e., anionic, lipids can also be incorporated into vesicular lipid bilayers to modify the (cationic) drug loading into or release from the resulting lipid aggregates. Attractive examples of such charged lipids are phosphatidylglycerols, phosphatidylinositols and, somewhat less preferred, phosphatidic acid (and its alkyl ester) or phosphatidylserine. It will be realised by anyone skilled in the art that it is less commendable to make vesicles just from the charged lipids than to use them in a combination with electroneutral bilayer component(s). In case of using charged lipids, buffer composition and/or pH care must selected so as to ensure the desired degree of lipid head-group ionization and/or the desired degree of electrostatic interaction between the, oppositely, charged drug and lipid molecules. Moreover, as with neutral lipids, the charged bilayer lipid components can in principle have any of the chains listed in the Table 1. The chains forming fluid phase lipid bilayers are clearly preferred, however, both due to vesicle adaptability increasing role of increasing fatty chain fluidity and due to better ability of lipids in fluid phase to mix with each other, and with drugs.

TABLE 2-continued

The (most) preferred basic, straight, saturated fatty chain residues

| Shorthand designation | Systematic name | Trivial name |
|---|---|---|
| 15:0 | Pentadecanoic | |
| 16:0 | Hexadecanoic | Palmitic |
| 17:0 | Heptadecanoic | Margaric |
| 18:0 | Octadecanoic | Stearic |
| 19:0 | Nonadecanoic | |
| 20:0 | Eicosanoic | Arachidic |
| 21:0 | Heneicosanoic | |
| 22:0 | Docosanoic | Behenic |
| 23:0 | Tricosanoic | |
| 24:0 | Tetracosanoic | Lignoceric |

TABLE 3

The (most) preferred monoenoic fatty chain residues

| Shorthand designation | Systematic name | Trivial name |
|---|---|---|
| 9-14:1/14:1(n-5) | cis-9-Tetradecenoic | Myristoleic |
| 7-16:1/16:1(n-9) | cis-7-Hexadecenoic | |
| 9-16:1/16:1(n-7) | cis-9-Hexadecenoic | Palmitoleic |
| 9-18:1/18:1(n-9) | cis-9-Octadecenoic | Oleic |

TABLE 3-continued

The (most) preferred monoenoic fatty chain residues

| Shorthand designation | Systematic name | Trivial name |
|---|---|---|
| 11-18:1/18:1(n-7) | cis-11-Octadecenoic | cis-Vaccenic |
| 11-20:1/20:1(n-9) | cis-11-Eicosenoic | Gondoic |
| 14-20:1/20:1(n-6) | cis-14-Eicosaenoic | |
| 13-22:1/22:1(n-9) | cis-13-Docosenoic | Erucic |
| 15-24:1/24:1(n-9) | cis-15-Tetracosenoic | Nervoni |
| 3t-18:1 | trans-3-Hexadecenoi | |
| 9t-18:1 | trans-9-Octadecenoic | Elaidic |
| 11t-18:1 | trans-11-Octadecenoic | Vaccenic |

TABLE 4

The (most) preferred dienoic and polyenoic fatty chain residues

| Shorthand designation | Systematic name | Trivial name |
|---|---|---|
| 10,13c-16:2/16:2(n-3) | 10-cis,13-cis-Hexadecadienoic | |
| 7,10c-16:2/16:3(n-6) | 7-cis,10-cis-Hexadecadienoic | |
| 7,10,13c-16:3/16:3(n-3) | 7-cis,10-cis,13-cis-Hexadecatrienoic | |
| 12,15c-18:2/18:2(n-3) | 12-cis,15-cis-Octadecadienoic | α-Linoleic |
| 10,12t-18:2/18:2(n-6) | trans-10,trans-12-Octadecadienoic | |
| 9,12c-18:2/18:2(n-6) | 9-cis,12-cis-Octadecadienoic | γ-Linoleic |
| 9,12,15c-18:3/18:3(n-3) | 9-cis,12-cis,15-cis-Octadecatrienoic | α-Linolenic |
| 6,9,12c-18:3/18:3(n-6) | 6-cis,9-cis,12-cis-Octadecatrienoic | γ-Linolenic |
| 9c,11c,13t-18:3 | 9-cis,11-trans,13-trans-Octadecatrienoic | α-Eleostearic |
| 8t,10t,12c-18:3 | 8-trans,10-trans,12-cis-Octadecatrienoic | Calendic |
| 6,9,12,15-18:4/18:4(n-3) | 6,9,12,15-Octadecatetraenoic | Stearidonic |
| 3,6,9,12c-18:4/18:4(n-6) | 3,6,9,12-Octadecatetraenoic | |
| 3,6,9,12,15c-18:5/18:5(n-3) | 3,6,9,12,15-Octadecapentaenoic | |
| 14,17c-20:2/20:2(n-3) | 14-cis,17-cis-Eicosadienoic | |
| 11,14c-20:2/20:2(n-6) | 11-cis,14-cis-Eicosadienoic | |
| 11,14,17c-20:3/20:3(n-3) | 8-cis,11-cis,14-cis-Eicosatrienoic | Dihomo-α-linolenic |
| 8,11,14c-20:3/20:3(n-6) | 8-cis,11-cis,14-cis-Eicosatrienoic | Dihomo-γ-linolenic |
| 5,8,11c-20:3 20:3(n-9) | 5,8,11all-cis-Eicosatrienoic | 'Mead's' |
| 5,8,11,14c-20:4/20:4(n-6) | 5,8,11; 14-all-cis-Eicosatetraenoic | Arachidonic |
| 8,11,14,17c-20:4/20:4(n-3) | 8,11,14,17-all-cis-Eicosatetraenoic | |
| 5,8,11,14,17c-20:5 or 20:5(n-3) | 5,8,11,14,17-all-cis-Eicosapentaenoic | |
| 13,16c-22:2 | 13,16-Docosadienoic | |
| 13,16,19c-22:3/22:3(n-3) | 13,16,19-Docosatrienoic | |
| 10,13,16c-22:3/22:3(n-6) | 10,13,16-Docosatrienoic | |
| 7,10,13,16c-22:4/22:4(n-6) | 7,10,13,16-Docosatetraenoic | Adrenic |
| 4,7,10,13,16c-22:5 or 22:5(n-6) | 4,7,10,13,16-Docosapentaenoic | |
| 4,7,10,13,16,19c-22:5 or 22:6(n-3) | 4,7,10,13,16,19-Docosahexaenoic | |

Other double bond combinations or positions are possible as well.

Suitable fatty residues can furthermore be branched, for example, can contain a methyl group in an iso or anteiso position of the fatty acid chain, or else closer to the chain middle, as in 10-R-Methyloctadecanoic acid or tuberculostearic chain. Relatively important amongst branched fatty acids are also isoprenoids, many of which are derived from 3,7,11,15-tetramethylhexadec-trans-2-en-1-ol, the aliphatic alcohol moiety of chlorophyll. Examples include 5,9,13,17-tetramethyloctadecanoic acid and especially 3,7,11,15-tetramethylhexadecanoic (phytanic) and 2,6,10,14-tetramethylpentadecanoic (pristanic) acids. A good source of 4,8,12-trimethyltridecanoic acid are marine organisms. Combination of double bonds and side chains on a fatty residue are also possible.

Alternatively, suitable fatty residues may carry one or a few oxy- or cyclic groups, especially in the middle or towards the end of a chain. The most prominent amongst the later, alicyclic fatty acids, are those comprising a cyclopropane (and sometimes cyclopropene) ring, but cyclohexyl and cycloheptyl rings can also be found and might be useful for purposes of this invention. 2-(D)-Hydroxy fatty acids are more ubiquitous than alicyclic fatty acids, and are also important constituents of sphingolipids. Also interesting are 15-hydroxy-hexadecanoic and 17-hydroxy-octadecanoic acids, and maybe 9-hydroxy-octadeca-trans-10,trans-12-dienoic (dimorphecolic) and 13-hydroxy-octadeca-cis-9,trans-11-dienoic (coriolic) acid. Arguably the most prominent hydroxyl-fatty acid in current pharmaceutical use is ricinoleic acid, (D-(−)12-hydroxy-octadec-cis-9-enoic acid, which comprises up to 90% of castor oil, which is also often used in hydrogenated form. Epoxy-methoxy-, and furanoid-fatty acids are of only limited practical interest in the context of this invention.

Generally speaking, unsaturation, branching or any other kind of derivatization of a fatty acid is best compatible with the intention of present invention of the site of such modification is in the middle or terminal part of a fatty acid chain. The cis-unsaturated fatty acids are also more preferable than trans-unsaturated fatty acids and the fatty radicals with fewer double bonds are preferred over those with multiple double bonds, due to oxidation sensitivity of the latter. Moreover, symmetric chain lipids are generally better suited than asymmetric chain lipids.

A preferred lipid of the formula III is, for example, a natural phosphatidylcholine, which used to be called lecithin. It can be obtained from egg (rich in palmitic, $C_{16:0}$, and oleic, $C_{18:1}$, but also comprising stearic, $C_{18:05}$ palmitoleic, $C_{16:1}$, linolenic, $C_{18:2}$, and arachidonic, $C_{20:4}$, radicals), soybean (rich in unsaturated $C_{18}$ chains, but also containing some palmitic radical, amongst a few others), coconut (rich in saturated chains), olives (rich in monounsaturated chains), saffron (safflower) and sunflowers (rich in n-6 linoleic acid), linseed (rich in n-3 linolenic acid), from whale fat (rich in monounsaturated n-3 chains), from primrose or primula (rich in n-3 chains). Preferred, natural phosphatidyl ethanolamines (used to be called cephalins) frequently originate from egg or soybeans. Preferred sphingomyelins of biological origin are typically prepared from eggs or brain tissue. Preferred phosphatidylserines also typically originate from brain material whereas phosphatidylglycerol is preferentially extracted from bacteria, such as *E. coli*, or else prepared by way of transphosphatidylation, using phospholipase D, starting with a natural phosphatidylcholine. The preferably used phosphatidylinositols are isolated from commercial soybean phospholipids or bovine liver extracts. The preferred phosphatidic acid is either extracted from any of the mentioned sources or prepared using phospholipase D from a suitable phosphatidylcholine.

Furthermore, synthetic phosphatidyl cholines ($R^4$ in formula III corresponds to 2-trimethylammonium ethyl), and $R^1$ and $R^2$ are aliphatic chains, as defined in the preceding paragraph with 12 to 30 carbon atoms, preferentially with 14 to 22 carbon atoms, and even more preferred with 16 to 20 carbon atoms, under the proviso that the chains must be chosen so as to ensure that the resulting ESAs comprise fluid lipid bilayers. This typically means use of relatively short saturated and of relatively longer unsaturated chains. Synthetic sphingomyelins ($R^4$ in formula IIIB corresponds to 2-trimethylammonium ethyl), and $R^1$ is an aliphatic chain, as defined in the preceding paragraph, with 10 to 20 carbon atoms, preferentially with 10 to 14 carbon atoms per fully saturated chain and with 16-20 carbon atoms per unsaturated chain.

Synthetic phosphatidyl ethanolamines ($R^4$ is 2-aminoethyl), synthetic phosphatidic acids ($R^4$ is a proton) or its ester ($R^4$ corresponds, for example, to a short-chain alkyl, such as methyl or ethyl), synthetic phosphatidyl serines ($R^4$ is L- or D-serine), or synthetic phosphatidyl (poly)alcohols, such as phosphatidyl inositol, phosphatidyl glycerol ($R^4$ is L- or D-glycerol) are preferred as lipids, wherein $R^1$ and $R^2$ are fatty residues of identical or moderately different type and length, especially such as given in the corresponding tables given before in the text. Moreover, $R^1$ can represent alkenyl and $R^2$ identical hydroxyalkyl groups, such as tetradecylhydroxy or hexadecylhydroxy, for example, in ditetradecyl or dihexadecylphosphatidyl choline or ethanolamine, $R^1$ can represent alkenyl and $R^2$ hydroxyacyl, such as a plasmalogen ($R^4$ trimethylammonium ethyl), or $R^1$ can be acyl, such as lauryl, myristoyl or palmitoyl and $R^2$ can represent hydroxy as, for example, in natural or synthetic lysophosphatidyl cholines or lysophosphatidyl glycerols or lysophosphatidyl ethanolamines, such as 1-myristoyl or 1-palmitoyllysophosphatidyl choline or -phosphatidyl ethanolamine; frequently, $R^3$ represents hydrogen.

A lipid of formula IIIB is also a suitable lipid within the sense of this invention. In formula IIIB, n=1, $R^1$ is an alkenyl group, $R^2$ is an acylamido group, $R^3$ is hydrogen and $R^4$ represents 2-trimethylammonium ethyl (choline group). Such a lipid is known under the name of sphingomyelin.

Suitable lipids furthermore are a lysophosphatidyl choline analog, such as 1-lauroyl-1,3-dihydroxypropane-3-phosphoryl choline, a monoglyceride, such as monoolein or monomyristin, a cerebroside, ceramide polyhexoside, sulfatide, sphingoplasmalogen, a ganglioside or a glyceride, which does not contain a free or esterified phosphoryl or phosphono or phosphino group in the 3 position. An example of such a glyceride is diacylglyceride or 1-alkenyl-1-hydroxy-2-acyl glyceride with any acyl or alkenyl groups, wherein the 3-hydroxy group is etherified by one of the carbohydrate groups named, for example, by a galactosyl group such as a monogalactosyl glycerin.

Lipids with desirable head or chain group properties can also be formed by biochemical means, for example, by means of phospholipases (such as phospholipase A1, A2, B, C and, in particular, D), desaturases, elongases, acyl transferases, etc., from natural or synthetic precursors.

Furthermore, a suitable lipid is any lipid, which is contained in biological membranes and can be extracted with the help of apolar organic solvents, such as chloroform. Aside from the lipids already mentioned, such lipids also include, for example, steroids, such as estradiol, or sterols, such as cholesterol, beta-sitosterol, desmosterol, 7-keto-cholesterol or beta-cholestanol, fat-soluble vitamins, such as retinoids, vitamins, such as vitamin A1 or A2, vitamin E, vitamin K, such as vitamin K1 or K2 or vitamin D1 or D3, etc.

The less soluble amphiphilic components comprise or preferably comprise a synthetic lipid, such as myristoleoyl, palmitoleoyl, petroselinyl, petroselaidyl, oleoyl, elaidyl, cis- or trans-vaccenoyl, linolyl, linolenyl, linolaidyl, octadecatetraenoyl, gondoyl, eicosaenoyl, eicosadienoyl, eicosatrienoyl, arachidoyl, cis- or trans-docosaenoyl, docosadienoyl, docosatrienoyl, docosatetraenoyl, lauroyl, tridecanoyl, myristoyl, pentadecanoyl, palmitoyl, heptadecanoyl, stearoyl or nonadecanoyl, glycerophospholipid or corresponding derivatives with branched chains or a corresponding dialkyl or sphingosin derivative, glycolipid or other diacyl or dialkyl lipid.

The more soluble amphiphilic components(s) is/are frequently derived from the less soluble components listed above and, to increase the solubility, substituted and/or complexed and/or associated with a butanoyl, pentanoyl, hexanoyl, heptanoyl, octanoyl, nonanoyl, decanoyl or undecanoyl substituent or several, mutually independent, selected substituents or with a different material for improving the solubility.

A further suitable lipid is a diacyl- or dialkyl-glycerophosphoetha-nolamine azo polyethoxylene derivative, a didecanoylphosphatidyl choline or a diacylphosphoolligomaltobionamide.

In certain embodiments, the amount of lipid in the formulation is from about 1% to about 10%, about 2% to about 10%, about 1% to about 4%, about 4% to about 7% or about 7% to about 10% by weight. In a specific embodiment, the lipid is a phospholipid. In another specific embodiment, the phospholipid is a phosphatidylcholine. In one embodiment, the topical formulations of the invention contain one or more antifungals (e.g., terbinafine), phosphatidylcholine and a surfactant, wherein the formulation contains 1-10% by weight of phosphatidylcholine.

4.3. Surfactant

The term "surfactant" has its usual meaning A list of relevant surfactants and surfactant related definitions is provided in EP 0 475 160 A1 (see, e.g., p. 6, 1. 5 to p. 14. 1.17) and U.S. Pat. No. 6,165,500 (see, e.g., col. 7, 1. 60 to col. 19, 1. 64) which are herewith incorporated by reference, and in appropriate surfactant or pharmaceutical Handbooks, such as Handbook of Industrial Surfactants or US Pharmacopoeia, Pharm. Eu. In some embodiments of the invention, the surfactants are those described in Tables 1-18 of U.S. Patent Application Publication No. 2002/0012680 A1, published Jan. 31, 2002, the disclosure of which is hereby incorporated by reference in its entirety. The following list therefore only offers a selection, which is by no means complete or exclusive, of several surfactant classes that are particularly common or useful in conjunction with present patent application. Preferred surfactants to be used in accordance with the invention include those with an HLB greater than 12. The list includes ionized long-chain fatty acids or long chain fatty alcohols, long chain fatty ammonium salts, such as alkyl- or alkenoyl-trimethyl-, -dimethyl- and -methyl-ammonium salts, alkyl- or alkenoyl-sulphate salts, long fatty chain dimethyl-aminoxides, such as alkyl- or alkenoyl-dimethyl-aminoxides, long fatty chain, for example alkanoyl, dimethyl-aminoxides and especially dodecyl dimethyl-aminoxide, long fatty chain, for example alkyl-N-methylglucamide-s and alkanoyl-N-methylglucamides, such as MEGA-8, MEGA-9 and MEGA-10, N-long fatty chain-N,N-dimethylglycines, for example N-alkyl-N,N-dimethylglycines, 3-(long fatty chain-dimethylammonio)-alkane-sulphonates, for example 3-(acyidimethylammonio)-alkanesulphonates, long fatty chain derivatives of sulphosuccinate salts, such as bis(2-ethylalkyl) sulphosuccinate salts, long fatty chain-sulphobetaines, for example acyl-sulphobetaines, long fatty chain betaines, such as EMPIGEN BB or ZWITTERGENT-3-16, -3-14, -3-12, -3-10, or -3-8, or polyethylen-glycol-acylphenyl ethers, especially nonaethylen-glycol-octyl-phenyl ether, polyethylene-long fatty chain-ethers, especially polyethylene-acyl ethers, such as nonaethylen-decyl ether, nonaethylen-dodecyl ether or octaethylene-dodecyl ether, polyethyleneglycol-isoacyl ethers, such as octaethyleneglycol-isotridecyl ether, polyethyleneglycol-sorbitane-long fatty chain esters, for example polyethyleneglycol-sorbitane-acyl esters and especially polyoxyethylene-monolaurate (e.g. polysorbate 20 or Tween 20), polyoxyethylene-sorbitan-monooleate (e.g. polysorbate 80 or Tween 80), polyoxyethylene-sorbitan-monolauroleylate, polyoxyethylene-sorbitan-monopetroselinate, polyoxyethylene-sorbitan-monoelaidate, polyoxyethylene-sorbitan-myristoleylate, polyoxyethylene-sorbitan-palmitoleinylate, polyoxyethylene-sorbitan-p-etroselinylate, polyhydroxyethylene-long fatty chain ethers, for example polyhydroxyethylene-acyl ethers, such as polyhydroxyethylene-lauryl ethers, polyhydroxyethylene-myristoyl ethers, polyhydroxyethylene-cetylst-earyl, polyhydroxyethylene-palmityl ethers, polyhydroxyethylene-oleoyl ethers, polyhydroxyethylene-palmitoleoyl ethers, polyhydroxyethylene-lino-leyl, polyhydroxyethylen-4, or 6, or 8, or 10, or 12-lauryl, miristoyl, palmitoyl, palmitoleyl, oleoyl or linoeyl ethers (Brij series), or in the corresponding esters, polyhydroxyethylen-laurate, -myristate, -palmitate, -stearate or -oleate, especially polyhydroxyethylen-8-stearate (Myrj 45) and polyhydroxyethylen-8-oleate, polyethoxylated castor oil 40 (Cremophor EL), sorbitane-mono long fatty chain, for example alkylate (Arlacel or Span series), especially as sorbitane-monolaurate (Arlacel 20, Span 20), long fatty chain, for example acyl-N-methylglucamides, alkanoyl-N-methylglucamides, especially decanoyl-N-methylglucamide, dodecanoyl-N-methylglucamide, long fatty chain sulphates, for example alkyl-sulphates, alkyl sulphate salts, such as lauryl-sulphate (SDS), oleoyl-sulphate; long fatty chain thioglucosides, such as alkylthioglucosides and especially heptyl-, octyl- and nonyl-beta-D-thioglucopyranoside; long fatty chain derivatives of various carbohydrates, such as pentoses, hexoses and disaccharides, especially alkyl-glucosides and maltosides, such as hexyl-, heptyl-, octyl-, nonyl- and decyl-beta-D-glucopyranoside or D-maltopyranoside; further a salt, especially a sodium salt, of cholate, deoxycholate, glycocholate, glycodeoxycholate, taurodeoxycholate, taurocholate, a fatty acid salt, especially oleate, elaidate, linoleate, laurate, or myristate, most often in sodium form, lysophospholipids, n-octadecylene-glycerophosphatidic acid, octadecylene-phosphorylglycerol, octadecylene-phosphorylserine, n-long fatty chain-glycero-phosphatidic acids, such as n-acyl-glycero-phosphatidic acids, especially lauryl glycero-phosphatidic acids, oleoyl-glycero-phosphatidic acid, n-long fatty chain-phosphorylglycerol, such as n-acyl-phosphorylglycerol, especially lauryl-, myristoyl-, oleoyl- or palmitoeloyl-phosphorylglycerol, n-long fatty chain-phosphorylserine, such as n-acyl-phosphorylserine, especially lauryl-, myristoyl-, oleoyl- or palmitoeloyl-phosphorylserine, n-tetradecyl-glycero-phosphatidic acid, n-tetradecyl-phosphorylglycerol, n-tetradecyl-phosphorylserine, corresponding-, elaidoyl-, vaccenyl-lysophospholipids, corresponding short-chain phospholipids, as well as all surface active and thus membrane destabilising polypeptides. Surfactant chains are typically chosen to be in a fluid state or at least to be compatible with the maintenance of fluid-chain state in carrier aggregates.

Table 5 lists preferred surfactants in accordance with the invention.

TABLE 5

Preferred nonionic surfactants for use in combination with antifungal

| | | | Nonionic surfactants (S) Head/Type/TM | | | |
|---|---|---|---|---|---|---|
| Name(s) | Fatty chain Length: nr. of double bonds | POE-sorbitan-ester Tween | POE-ether Brij, Macrogol | POE-ester Myrj, Nonex | POE-phenoxy-ether Triton | Selected brandnames |
| Behen(o)yl | C24 C22 | | | | | |
| Eruca(o)yl | C22:1-13cis | | | | | |
| Arachin(o)yl | C20 | | | | | |
| Gadolen(o)yl | C20:1-11cis | | | | | |
| Arachidon(o)yl | C20:4-5,8,11,14cis | | | | | |
| Ole(o)yl | C18:1-9cis | Tween 80 | Brij 98 | Simulsol-2599 | TritonX100** | |
| Stear(o)yl | C18 | Tween 60 | | Myrj-52 | | |
| Linol(o)yl | C18:2-9,12cis | | | | | |
| Linole(n/o)yl | C18:3-9,12,15cis | | | | | |
| Palmitole(o)yl | C18:1-9cis | | | | | |
| Palmit(o)yl | C16 | Tween 40 | | NN | | |
| Myrist(o)yl | C14 | | | | | |
| Laur(o)yl | C12 | Tween 20 | Brij 35 | NN | | |

TABLE 5-continued

Preferred nonionic surfactants for use in combination with antifungal

| | | Nonionic surfactants (S) Head/Type/TM | | | | |
|---|---|---|---|---|---|---|
| Fatty chain | | | | | | |
| Name(s) | Length: nr. of double bonds | POE-sorbitan-ester Tween | POE-ether Brij, Macrogol | POE-ester Myrj, Nonex | POE-phenoxy-ether Triton | Selected brandnames |
| Capr(o)yl | C10 | | | | | |
| Rel. concentration range L/S (M/M) | | 5/1–1/1 | 5/1–1/1 | 5/1–1/1 | 4/1–3/2 | |

NN: not readily available in the market but in principle suitable
**Triton is not an oleate, but an octylphenoxy-POE derivative
Myrj-45: Stearoyl-EO8;
Myrj-49: Stearoyl-EO20 (not in the market);
Myrj-59: Stearoyl-EO100; Myrj-52: Stearoyl-EO40;
Simulsol-2599 = Macrogol-10-oleate
Brij-98: Oleoyl-EO20
Brij-35: Lauryl-EO23

In certain embodiments, the surfactant is a nonionic surfactant. The surfactant may be present in the formulation in about 1% to about 10%, about 1% to about 4%, about 4% to about 7% or about 7% to about 10% by weight. In certain embodiments, the nonionic surfactant is selected from the group consisting of: polyoxyethylene sorbitans (polysobate surfactants), polyhydroxyethylene stearates or polyhydroxyethylene laurylethers (Brij surfactants). In a specific embodiment, the surfactant is a polyoxyethylene-sorbitan-monooleate (e.g. polysorbate 80 or Tween 80).

4.4. Formulations

The antifungal formulations of the invention may contain 1 to 10% by weight, 1 to 15% by weight, 1 to 20% by weight, or 1 to 30% antifungal by weight. The topical antifungal formulations of the invention may contain 1 to 10% by weight, 1 to 15% by weight, 1 to 20% by weight, or 1 to 30% lipid by weight. The antifungal formulations of the invention may contain 1 to 10% by weight, 1 to 15% by weight, 1 to 20% by weight, 1 to 30% by weight, 1 to 40% by weight or 1 to 50% surfactant by weight.

The antifungal formulations of the invention may have a range of lipid to surfactant ratios. The ratios may be expressed in terms of molar terms (mol lipid/mol surfactant). The molar ratio of lipid to surfactant in the antifungal formulations of the invention may be from about 1:2 to about 10:1. In certain embodiments, the ratio is from about 1:1 to about 5:1, about 1:1 to about 2:1, from about 2:1 to about 3:1, from about 3:1 to about 4:1, from about 4:1 to about 5:1 or from about 5:1 to about 10:1. In specific embodiments, the lipid to surfactant ratio is about 1.0:1.0, about 1.25:1.0, about 1.5/1.0, about 1.75/1.0, about 2.0/1.0, about 2.5/1.0, about 3.0/1.0 or about 4.0/1.0.

The antifungal formulations of the invention may have varying ratios of antifungal to lipid. The ratios may be expressed in terms of molar ratios (mol antifungal/mol lipid). The molar ratio of antifungal to lipid in the topical antifungal formulations of the invention may be from about 0.2:1 to about 2:1. In certain embodiments, the ratio is from about 0.2:1 to about 0.7:1, from about 0.7:1 to about 1.2:1, from about 1.2:1 to about 1.7:1 or from about 1.7:1 to about 2:1.

The antifungal formulations of the invention may also have varying amounts of total amount of the following three components: antifungal, lipid and surfactant combined (TA). The TA amount may be stated in terms of weight percent of the total composition. In one embodiment, the TA is from about 1% to about 40%, about 5% to about 30%, about 7.5% to about 15%, about 5% to about 10%, about 10% to about 20% or about 20% to about 30%. In specific embodiments, the TA is 8%, 9%, 10%, 15% or 20%.

Selected ranges for total lipid amounts, lipid/surfactant ratios (mol/mol) and antifungal/surfactant ratios (mol/mol) for topical antifungal formulations of the invention are described in Table 6 below:

TABLE 6

Total Lipid, Lipid to Surfactant Ratios and Antifungal to Lipid Ratios

| TA (antifungal, lipid and surfactant) (%) | Lipid/Surfactant (mol/mol) | Antifungal/Lipid (mol/mol) |
|---|---|---|
| 5 to 10 | 1.0 to 1.25 | 0.20 to 0.75 |
| 5 to 10 | 1.0 to 1.25 | 0.75 to 1.25 |
| 5 to 10 | 1.0 to 1.25 | 1.25 to 2.00 |
| 5 to 10 | 1.25 to 1.75 | 0.20 to 0.75 |
| 5 to 10 | 1.25 to 1.75 | 0.75 to 1.25 |
| 5 to 10 | 1.25 to 1.75 | 1.25 to 2.00 |
| 5 to 10 | 1.75 to 2.25 | 0.20 to 0.75 |
| 5 to 10 | 1.75 to 2.25 | 0.75 to 1.25 |
| 5 to 10 | 1.75 to 2.25 | 1.25 to 2.00 |
| 5 to 10 | 2.25 to 3.00 | 0.20 to 0.75 |
| 5 to 10 | 2.25 to 3.00 | 0.75 to 1.25 |
| 5 to 10 | 2.25 to 3.00 | 1.25 to 2.00 |
| 5 to 10 | 2.25 to 3.00 | 2.00 to 2.25 |
| 5 to 10 | 3.00 to 4.00 | 0.20 to 0.75 |
| 5 to 10 | 3.00 to 4.00 | 0.75 to 1.25 |
| 5 to 10 | 3.00 to 4.00 | 1.25 to 2.00 |
| 5 to 10 | 3.00 to 4.00 | 2.00 to 2.25 |
| 10 to 20 | 1.0 to 1.25 | 0.20 to 0.75 |
| 10 to 20 | 1.0 to 1.25 | 0.75 to 1.25 |
| 10 to 20 | 1.0 to 1.25 | 1.25 to 2.00 |
| 10 to 20 | 1.25 to 1.75 | 0.20 to 0.75 |
| 10 to 20 | 1.25 to 1.75 | 0.75 to 1.25 |
| 10 to 20 | 1.25 to 1.75 | 1.25 to 2.00 |
| 10 to 20 | 1.75 to 2.25 | 0.20 to 0.75 |
| 10 to 20 | 1.75 to 2.25 | 0.75 to 1.25 |
| 10 to 20 | 1.75 to 2.25 | 1.25 to 2.00 |
| 10 to 20 | 2.25 to 3.00 | 0.20 to 0.75 |
| 10 to 20 | 2.25 to 3.00 | 0.75 to 1.25 |
| 10 to 20 | 2.25 to 3.00 | 1.25 to 2.00 |
| 10 to 20 | 2.25 to 3.00 | 2.00 to 2.50 |
| 10 to 20 | 3.00 to 4.00 | 0.20 to 0.75 |
| 10 to 20 | 3.00 to 4.00 | 0.75 to 1.25 |
| 10 to 20 | 3.00 to 4.00 | 1.25 to 2.00 |
| 10 to 20 | 3.00 to 4.00 | 2.00 to 2.50 |

The antifungal formulations of the invention may optionally contain one or more of the following ingredients: co-solvents, chelators, buffers, antioxidants, preservatives, microbicides, emollients, humectants, lubricants and thickeners. Preferred amounts of optional components are described in Table 7.

The antifungal formulations of the invention may include a buffer to adjust the pH of the aqueous solution to a range from pH 3.5 to pH 9, pH 4 to pH 7.5, or pH 4 to pH 6.5. Examples of buffers include, but are not limited to, acetate buffers, lactate buffers, phosphate buffers, and propionate buffers.

The antifungal formulations of the invention is typically formulated in aqueous media. The formulations may be formulated with or without co-solvents, such as lower alcohols.

A "microbicide" or "antimicrobial" agent is commonly added to reduce the bacterial count in pharmaceutical formulations. Some examples of microbicides are short chain alcohols, including ethyl and isopropyl alcohol, chlorbutanol, benzyl alcohol, chlorbenzyl alcohol, dichlorbenzylalcohol, hexachlorophene; phenolic compounds, such as cresol, 4-chloro-m-cresol, p-chloro-m-xylenol, dichlorophene, hexachlorophene, povidon-iodine; parabenes, especially alkyl-parabenes, such as methyl-, ethyl-, propyl-, or butyl-paraben, benzyl paraben; acids, such as sorbic acid, benzoic acid and their salts; quaternary ammonium compounds, such as alkonium salts, e.g., a bromide, benzalkonium salts, such as a chloride or a bromide, cetrimonium salts, e.g., a bromide, phenoalkecinium salts, such as phenododecinium bromide, cetylpyridinium chloride and other salts; furthermore, mercurial compounds, such as phenylmercuric acetate, borate, or nitrate, thiomersal, chlorhexidine or its gluconate, or any antibiotically active compounds of biological origin, or any suitable mixture thereof.

Examples of "antioxidants" are butylated hydroxyanisol (BHA), butylated hydroxytoluene (BHT) and di-tert-butylphenol (LY178002, LY256548, HWA-131, BF-389, CI-986, PD-127443, E-5119, BI-L-239XX, etc.), tertiary butylhydroquinone (TBHQ), propyl gallate (PG), 1-O-hexyl-2,3,5-trimethylhydroquinone (HTHQ); aromatic amines (diphenylamine, p-alkylthio-o-anisidine, ethylenediamine derivatives, carbazol, tetrahydroindenoindol); phenols and phenolic acids (guaiacol, hydroquinone, vanillin, gallic acids and their esters, protocatechuic acid, quinic acid, syringic acid, ellagic acid, salicylic acid, nordihydroguaiaretic acid (NDGA), eugenol); tocopherols (including tocopherols (alpha, beta, gamma, delta) and their derivatives, such as tocopheryl-acylate (e.g., -acetate, -laurate, myristate, -palmitate, -oleate, -linoleate, etc., or an y other suitable tocopheryl-lipoate), tocopheryl-POE-succinate; trolox and corresponding amide and thiocarboxamide analogues; ascorbic acid and its salts, isoascorbate, (2 or 3 or 6)-o-alkylascorbic acids, ascorbyl esters (e.g., 6-o-lauroyl, myristoyl, palmitoyl-, oleoyl, or linoleoyl-L-ascorbic acid, etc.). Also useful are the preferentially oxidised compounds, such as sodium bisulphite, sodium metabisulphite, thiourea; chellating agents, such as EDTA, GDTA, desferral; miscellaneous endogenous defence systems, such as transferrin, lactoferrin, ferritin, cearuloplasmin, haptoglobion, heamopexin, albumin, glucose, ubiquinol-10); enzymatic antioxidants, such as superoxide dismutase and metal complexes with a similar activity, including catalase, glutathione peroxidase, and less complex molecules, such as beta-carotene, bilirubin, uric acid; flavonoids (flavones, flavonols, flavonones, flavanonals, chacones, anthocyanins), N-acetylcystein, mesna, glutathione, thiohistidine derivatives, triazoles; tannines, cinnamic acid, hydroxycinnamatic acids and their esters (coumaric acids and esters, caffeic acid and their esters, ferulic acid, (iso-) chlorogenic acid, sinapic acid); spice extracts (e.g., from clove, cinnamon, sage, rosemary, mace, oregano, allspice, nutmeg); carnosic acid, carnosol, carsolic acid; rosmarinic acid, rosmaridiphenol, gentisic acid, ferulic acid; oat flour extracts, such as avenanthramide 1 and 2; thioethers, dithioethers, sulphoxides, tetralkylthiuram disulphides; phytic acid, steroid derivatives (e.g., U74006F); tryptophan metabolites (e.g., 3-hydroxykynurenine, 3-hydroxyanthranilic acid), and organochalcogenides.

"Thickeners" are used to increase the viscosity of pharmaceutical formulations to and may be selected from selected from pharmaceutically acceptable hydrophilic polymers, such as partially etherified cellulose derivatives, comprising carboxymethyl-, hydroxyethyl-, hydroxypropyl-, hydroxypropylmethyl- or methyl-cellulose; completely synthetic hydrophilic polymers comprising polyacrylates, polymethacrylates, poly(hydroxyethyl)-, poly(hydroxypropyl)-, poly(hydroxypropylmethyl)methacrylate, polyacrylonitrile, methallyl-sulphonate, polyethylenes, polyoxiethylenes, polyethylene glycols, polyethylene glycol-lactide, polyethylene glycol-diacrylate, polyvinylpyrrolidone, polyvinyl alcohols, poly(propylmethacrylamide), poly(propylene fumarate-co-ethylene glycol), poloxamers, polyaspartamide, (hydrazine cross-linked) hyaluronic acid, silicone; natural gums comprising alginates, carrageenan, guar-gum, gelatine, tragacanth, (amidated) pectin, xanthan, chitosan collagen, agarose; mixtures and further derivatives or co-polymers thereof and/or other pharmaceutically, or at least biologically, acceptable polymers.

The antifungal formulations of the present invention may also comprise a polar liquid medium. The topical antifungal formulations of the invention may be administered in an aqueous medium. The antifungal formulations of the present invention may be in the form of a solution, suspension, emulsion, cream, lotion, ointment, gel, spray, film forming solution or lacquer.

In one embodiment, the invention specifically relates to the use of antifungal, a phospholipid and a nonionic surfactant for the preparation of a pharmaceutical composition for treating onychomycosis. In this context, the invention relates to a formulation or pharmaceutical composition comprising antifungal for the treatment of onychomycosis wherein the formulation or pharmaceutical composition is formulated for topical delivery.

Table 7 lists preferred excipients for the formulation.

TABLE 7

Preferred excipients for use in combinations with antifungal
Designated activity

| Antioxydant | Molar (M) or Rel. w %* | Antibiotic | Molar (M) or Weight-% | Buffer | Molar |
|---|---|---|---|---|---|
| Primary | | Acetate | 30-150 mM | Acetate | 30-150 mM |
| Butylated hydroxyanisole, BHA | 0.1-8 | Benzyl alcohol | 0.1-3 | Phosphate | 10-50 mM |
| Butylated hydroxytoluene, BHT | 0.1-4 | Butylparabene | 0.1-3 | Triethanolamine•HCL | 30-150 mM |

TABLE 7-continued

Preferred excipients for use in combinations with antifungal
Designated activity

| Antioxydant | Molar (M) or Rel. w %* | Antibiotic | Molar (M) or Weight-% | Buffer | Molar |
|---|---|---|---|---|---|
| Thymol | 0.1-1 | Ethylparabene | 0.1-3 | | |
| Metabisulphite (MW = 190.1) | 1-5 mM | Imidurea (MW = 388.30) | 0.1-1 | | |
| Bisulphite | 1-5 mM | Dimethoxane (MW = 174.2) | 0.03-0.1 | | |
| Thiourea (MW = 76.12) | 1-10 mM | | | | |
| Monothioglycerol (MW = 108.16) | 1-20 mM | Methylparabene | 0.1-5 | | |
| Propyl gallate (MW = 212.2) | 0.02-0.2 | Phenoxyethanol | 0.1-5 | | |
| Ascorbate (MW = 175.3 + ion) | 1-10 mM | Benzalkonium chloride | 0.01-0.2 | | |
| Palmityl-ascorbate | 0.01-1 | Benzethonium chloride | 0.01-0.1 | | |
| Tocopherol-PEG | 0.5-5 | Phenol | 0.05-2 | | |
| Secondary (chelator) | | Phenylethyl alcohol | 0.1-1 | | |
| EDTA (MW = 292) | 1-10 mM | Thimerosal | 0.005-0.1 | | |
| EGTA (MW = 380.35) | 1-10 mM | | | | |
| Desferal (MW = 656.79) | 0.1-5 mM | | | | |

*As percentage of Total Lipid quantity
EGTA = Ethylene glycol-bis-(2-aminoethyl)-N,N,N',N'-tetraacetic acid
EDTA = Ethylenedioxy-diethylene-dinitrilo-tetraacetic acid 4.4. Vesicular Formulations While not to be limited to any mechanism of action or any theory, the formulations of the invention may form vesicles or ESAs characterized by their adaptability, deformability, or penetrability.

The term vesicle or aggregate "adaptability" which governs the "tolerable surface curvature" is defined as the ability of a given vesicle or aggregate to change easily its properties, such as shape, elongation ratio, and surface to volume ratio. The vesicles of this invention may be characterized by their ability to adjust the aggregates' shape and properties to the anisotropic stress caused by pore crossing. Sufficient adaptability implies that a vesicle or an aggregate can sustain different unidirectional forces or stress, such as one caused by pressure, without extensive fragmentation, which defines a "stable" aggregate. If an aggregate passes through a barrier fulfilling this condition the terms "adaptability" and (shape) "deformability" plus "permeability" are essentially equivalent. A "barrier" in the context of this invention is (as in, for example, EP 0 475 160 and WO 98/17255) a body with through-extending narrow pores, such narrow pores having a radius which is at least 25% smaller than the radius of the ESAs (considered as spherical) before said ESAs permeate through such pores.

The term "narrow" used in connection with a pore implies that the pore radius is significantly, typically at least 25%, smaller than the radius of the entity tested with regard to its ability to cross the pore. The necessary difference typically should be greater for the narrower pores. Using 25% limit is therefore quite suitable for >150 nm diameter whereas >100% difference requirement is more appropriate for the smaller systems, e.g., with <50 nm diameter. For diameters around 20 nm, aggregate diameter difference of at least 200% is often required.

The term "semipermeable" used in connection with a barrier implies that a solution can cross transbarrier openings whereas a suspension of non-adaptable aggregates (large enough for the above definition of "narrow" pores to apply) cannot. Conventional lipid vesicles (liposomes) made from any common phosphatidylcholine in the gel lamellar phase or else from any biological phosphatidylcholine/cholesterol 1/1 mol/mol mixture or else comparably large oil droplets, all having the specified relative diameter, are three examples for such non-adaptable aggregates.

The term "stable" means that the tested aggregates do not change their diameter spontaneously or under the transport related mechanical stress (e.g. during passage through a semi-permeable barrier) unacceptably, which most often means only to a pharmaceutically acceptable degree. A 20-40% change is normally considered acceptable; the halving or doubling of aggregate diameter is borderline and a greater change in diameter is typically unacceptable. Alternatively and very conveniently, the change in aggregate diameter resulting from pore crossing under pressure is used to assess system stability; the same criteria are then applied as for "narrow" pores, mutatis mutandis. To obtain the correct value for aggregate diameter change, a correction for flux/vortex effects may be necessary. These procedures are described in greater detail in the publications of the applicant in Cevc et. al., Biochim. Biophys. Acta 2002; 1564:21-30.

Non-destructing passage of ultradeformable, mixed lipid aggregates through narrow pores in a semi-permeable barrier is thus diagnostic of high aggregate adaptability. If pore radius is two times smaller than the average aggregate radius the aggregate must change its shape and surface-to-volume ratio at least 100% to pass without fragmentation through the barrier. An easy and reversible change in aggregate shape inevitably implies high aggregate deformability and requires large surface-to-volume ratio adaptation. A change in surface-to-volume ratio per se implies: a) high volume compressibility, e.g. in the case of compact droplets containing material other than, and immiscible with, the suspending fluid; b) high aggregate membrane permeability, e.g. in the case of vesicles that are free to exchange fluid between inner and outer vesicle volume.

4.5 Methods of Administration

Another aspect of the invention provides methods of administering a pharmaceutical composition comprising antifungal, a lipid, and a surfactant. Generally, the pharmaceutical composition is administered to nail tissue. For instance, in some embodiments, it is administered topically to the nail tissue.

As used herein, the term "nail tissue," is used to describe any tissue that is a component of the "nail unit." The nail unit is comprised of the matrix, the nail plate, the nail bed, the cuticle, the lunula and the hyponychium. The matrix is where the cells multiply and keratinize before being incorporated into the nail plate. This tissue starts about 5 mm proximal to the nail fold and covers all the area called "lunula" or "half moon". The matrix is protected from infection by the cuticle, a fold of modified stratum corneum proximal to the nail plate.

In one embodiment, the topical formulation is administered to nail tissue and/or surrounding skin of a human subject which results in a mean concentration of antifungal per gram of nail tissue of about at least 1.5 mg/g, 2.0 mg/g, 2.1 mg/g, 2.2 mg/g, 2.3 mg/g, 2.4 mg/g, 2.5 mg/g, 2.6 mg/g, 2.7 mg/g, 2.8 mg/g, 2.9 mg/g and 3.0 mg/g. In another embodiment, the topical formulation is administered to nail tissue of a human subject which results in a mean concentration of antifungal per gram of nail tissue of about 0.1 to about 15 mg/g, about 0.2 to about 12.5 mg/g, about 0.5 to about 10.0 mg/g, about 1.0 to about 7.5 mg/g or about 2.0 to about 5.0 mg/g. The mean concentration can be determined one, two or three weeks after ceasing administration of the topical formulation. The invention also provides a method of treating a fungal infection of nail tissue in a human subject comprising administering a topical formulation to the infected nail tissue and/or surrounding skin of the human subject which results in a mean concentration of antifungal per gram of nail tissue of about 0.1 to about 15 mg/g, about 0.2 to about 12.5 mg/g, about 0.5 to about 10.0 mg/g, about 1.0 to about 7.5 mg/g or about 2.0 to about 5.0 mg/g. The mean concentration can be determined one, two or three weeks after ceasing administration of the pharmaceutical composition.

In certain embodiments of the methods, the administration of topical antifungal formulations of the invention also results in a mean serum concentration of antifungal in the human subject of less than 10.0 ng/ml, 5.0 ng/ml, 4.0 ng/ml, 3.0 ng/ml, 2.0 ng/ml, 1.0 ng/ml, 0.5 ng/ml or 0.2 ng/ml.

In some embodiments of the methods, the topical formulation comprises about 1.0 to about 5.0 mg of antifungal. In a specific embodiment of the method, the pharmaceutical composition comprises 3.0 mg of antifungal. The topical formulation can be administered, for example, twice daily. In certain embodiments, the composition may also be administered, once every two days, once daily, three times a day or four times a day. In certain embodiments, the topical formulation is administered for at least three weeks. In other embodiments, the topical formulation is administered for 3 to 48 weeks, 3 to 36 weeks or 3 to 24 weeks, 3 to 12 weeks or 3 to 6 weeks.

In a specific embodiment of the methods, the topical formulation is administered for 12 weeks to treat nail fungal infection, followed by an assessment to determine whether a mycological cure has been achieved. If a mycological cure has been achieved, further administration of the topical formulation is ceased. If a mycological cure has not been achieved, then the topical formulation is again administered for another 12 week period, followed by a second assessment to determine whether the regiment has achieved a cure. The cycle can be repeated until the regimen achieves a mycological cure. In certain embodiments, the formulations are adapted to cause a greater than 90% mycological cure rate.

In another embodiment, a topical formulation comprising antifungal, a lipid, and a surfactant is administered to nail tissue and/or surrounding skin twice daily for at least one, two or three weeks. The invention also provides a method of treating a fungal infection of nail tissue in a human subject comprising administering a topical formulation to the infected nail tissue and surrounding skin of the human subject twice daily for at least one, two or three weeks, wherein the topical formulation comprises antifungal, a lipid, and a surfactant.

In certain embodiments of the methods, the topical formulation may also be administered, once every two days, daily, three times a day or four times a day. In specific embodiments, the topical formulation is administered for 3 to 48 weeks, 3 to 36 weeks, 3 to 24 weeks, 3 to 12 weeks or 3 to 6 weeks.

In some embodiments of the methods, the topical formulation comprises from about 1.0 to about 5.0 mg of antifungal. For instance, the topical formulation can comprise about 3.0 mg of antifungal.

In a particular embodiment, the fungal infection being treated comprises onychomycosis.

In some embodiments of the methods described herein, the topical formulation is administered for a period longer than 12 weeks. For instance, in some embodiments, the topical formulation is administered for at least 24 weeks, for at least 36 weeks, or for at least 48 weeks.

In some embodiments of the methods, a cyclical treatment regimen is employed. Such regimens employ treatment cycles involving the administration of the topical formulation for a period of time, followed by a period wherein no formulation is administered, and, if necessary, repeating this sequence, i.e., the cycle. Treatment cycles can include, for example, administering, the topical formulation consecutively for a period of 12 weeks, e.g., using twice daily administration, followed a period of time wherein no formulation is administered, followed by another period where the formulation is again administered consecutively for another 12 weeks.

Certain embodiments of the methods include treatment regimens, wherein the topical formulation is administered to treat nail fungal infection for a period of time, followed by an assessment of the subject to determine whether the administration has achieved a mycological cure in the subject. If a mycological cure has been achieved, further administration of the topical formulation is ceased. If a mycological cure has not been achieved, then the topical formulation is again administered during a second administration period, which is followed by a second assessment to determine whether the regimen has achieved a cure. The cycle can be repeated until the regimen achieves a mycological cure.

In certain embodiments, the invention relates to using the methods of administration described herein to treat specific patient populations. In some embodiments, a population of patients who suffer chronically from nail fungal infection can be treated with the methods of administration described herein. In a specific embodiment, a population of patients who suffer from persistent re-infection can be treated using the methods described herein. For instance, the topical formulation may be administered to such a population during first administration period, (e.g., a first 12 week period) and then again for a second subsequent administration period (e.g., an additional 12 week period) to prevent re-infection of nail tissue.

In other embodiments, the methods of administration described herein may be used prophylactically in order to prevent re-infection of nail tissue in a population of patients who suffer chronically from nail fungal infections.

4.5 Kits

The invention further includes a pharmaceutical pack or kit comprising one or more containers filled with a antifungal formulation of the invention for the treatment or prevention of a fungal infection in a human subject. The invention provides kits that can be used in the above-described methods.

In one embodiment, a kit comprises one or more containers comprising an antifungal formulation of the invention. The kit may further comprise instructions for administering the antifungal formulations of the invention for the treating or preventing skin and/or nail infections, as well as side effects and dosage information. Optionally associated with such container(s) can be a notice in the form prescribed by a governmental agency regulating the manufacture, use or sale for human administration.

5. EXAMPLES

5.1 Example 1

Antifungal Formulations

Antifungal formulations for topical application may be prepared by the following procedure:

1. Organic Phase Production, which Contains all Lipophilic Excipients

The organic phase is produced by weighing the lipid, the surfactant, antifungal hydrochloride and any additional lipophilic excipients into suitable containers followed by mixing these components into anoptically isotropic phase which appears as a clear solution. During mixing, the organic phase will be heated up, but temperature must not rise above 45° C.

2. Aqueous Phase Production

The aqueous phase is prepared by weighing the non-lipophilic components and water, which serves as solvent, into suitable containers and then mixing these components into a clear solution. During mixing, the temperature will be elevated to 40° C.

3. Production of a Concentrated Intermediate by Combination of Both Phases

The isotropic organic phase and the clear aqueous phase are combined under stirring in a suitable vessel. Before and during the combination the temperature of both phases must be kept between 35° C. and 45° C. The resulting intermediate is homogenised mechanically at 40° C. Before starting homogenisation, the pressure in the production vessel is lowered to −0.08 MPa. The desired average carrier size is typically reached after 10 minutes of homogenisation.

Three process parameters must be controlled carefully during the production of the concentrated intermediate: temperature, homogeniser circulation velocity, and overall processing time.

4. Production of the Final Bulk Product by Mixing the Concentrated Intermediate with Dilution Buffer.

The concentrated intermediate is diluted with the dilution buffer to the intended final concentration. The mixture is carefully stirred in the mixing vessel at 20° C. to homogeneity.

Table 8 describes the amount of surfactant, lipid, and one or more antifungal (e.g., terbinafine) in preferred antifungal formulations of the invention. The amount of one or more antifungal, lipid, lipid and surfactant combined is described in terms of the percent total in the formulation. One of the terbinafine formulations described below was tested for efficacy in vivo.

TABLE 8

Preferred Antifungal Formulations of the Invention

Table 8A: This table lists the relative amounts of each of the components of Preferred Antifungal Formulations of the Invention

| | antifungal (1-50 mg/g) | Lipid mg/g (1 to 10% by wt.) | Surfactant mg/g (1 to 10% by wt.) | Buffer (pH 4-7.5) | Antimicrobials (0-10 mg/g) | Antioxidants (0-10 mg/g) | Emollient (0-50 mg/g) | Other (0-50 mg/g) | Chelator (0-25 mg/g) |
|---|---|---|---|---|---|---|---|---|---|
| 1 | 10 | 47.944 | 42.056 | 4 | 5.250 | 0.700 | 30.000 | 30.000 | 3.000 |
| 2 | 15 | 53.750 | 31.250 | 4 | 5.250 | 0.700 | 30.000 | 15.000 | 3.000 |
| 3 | 30 | 90.561 | 79.439 | 4 | 5.250 | 0.700 | 30.000 | 30.000 | 3.000 |
| 4 | 10 | 47.944 | 42.056 | 5 | 5.250 | 0.700 | 30.000 | 30.000 | 3.000 |
| 5 | 5 | 50.607 | 44.393 | 5 | 5.250 | 0.700 | 0.000 | 10.000 | 3.000 |
| 6 | 30 | 90.561 | 79.439 | 5 | 5.250 | 0.700 | 30.000 | 30.000 | 3.000 |
| 7 | 7.5 | 49.276 | 43.224 | 6.5 | 5.250 | 0.700 | 30.000 | 30.000 | 3.000 |
| 8 | 15 | 53.750 | 31.250 | 6.5 | 5.250 | 0.200 | 30.000 | 0.000 | 3.000 |
| 9 | 30 | 90.561 | 79.439 | 6.5 | 5.250 | 0.200 | 30.000 | 20.000 | 3.000 |
| 10 | 10 | 41.351 | 48.649 | 4 | 5.250 | 0.200 | 30.000 | 30.000 | 3.000 |
| 11 | 15 | 47.882 | 37.118 | 4 | 5.250 | 0.200 | 0.000 | 30.000 | 3.000 |
| 12 | 30 | 95.764 | 74.236 | 4 | 5.250 | 0.200 | 30.000 | 30.000 | 3.000 |
| 13 | 10 | 65.676 | 24.324 | 5 | 5.250 | 0.200 | 0.000 | 25.000 | 3.000 |
| 14 | 15 | 62.027 | 22.973 | 5 | 5.250 | 0.200 | 0.000 | 30.000 | 3.000 |
| 15 | 30 | 124.054 | 45.946 | 5 | 5.250 | 0.200 | 15.000 | 30.000 | 3.000 |
| 16 | 5 | 62.687 | 32.313 | 6.5 | 5.250 | 0.200 | 15.000 | 0.000 | 3.000 |
| 17 | 15 | 41.853 | 43.147 | 6.5 | 5.250 | 0.200 | 30.000 | 30.000 | 3.000 |
| 18 | 30 | 95.764 | 74.236 | 6.5 | 5.250 | 0.200 | 0.000 | 30.000 | 3.000 |
| 19 | 15 | 47.882 | 37.118 | 6.5 | 5.250 | 0.200 | 0.000 | 0.000 | 3.000 |
| 20 | 10 | 45.000 | 45.000 | 6.5 | 5.250 | 0.200 | 0.000 | 0.000 | 3.000 |
| 21 | 10 | 31.935 | 58.065 | 5 | 5.250 | 0.200 | 30.000 | 15.000 | 3.000 |
| 22 | 15 | 42.500 | 42.500 | 6.5 | 5.250 | 0.200 | 30.000 | 0.000 | 3.000 |
| 23 | 10 | 38.276 | 51.724 | 4 | 5.250 | 0.200 | 0.000 | 30.000 | 3.000 |
| 24 | 15 | 42.500 | 42.500 | 4 | 5.250 | 0.200 | 0.000 | 15.000 | 3.000 |
| 25 | 30 | 85.000 | 85.000 | 4 | 5.250 | 0.200 | 30.000 | 30.000 | 3.000 |
| 26 | 10 | 38.276 | 51.724 | 5 | 5.250 | 0.200 | 30.000 | 0.000 | 3.000 |
| 27 | 15 | 36.429 | 48.571 | 5 | 5.250 | 0.200 | 30.000 | 30.000 | 3.000 |
| 28 | 30 | 72.299 | 97.701 | 5 | 5.250 | 0.200 | 30.000 | 15.000 | 3.000 |

TABLE 8-continued

Preferred Antifungal Formulations of the Invention

| | | | | | | | | | |
|---|---|---|---|---|---|---|---|---|---|
| 29 | 7.5 | 46.250 | 46.250 | 6.5 | 5.250 | 0.700 | 0.000 | 20.000 | 3.000 |
| 30 | 15 | 38.804 | 46.196 | 6.5 | 5.250 | 0.700 | 15.000 | 30.000 | 3.000 |
| 31 | 30 | 36.667 | 33.333 | 6.5 | 5.250 | 0.700 | 30.000 | 10.000 | 3.000 |
| 32 | 10 | 66.667 | 23.333 | 4 | 5.250 | 0.200 | 0.000 | 0.000 | 3.000 |
| 33 | 12.5 | 45.833 | 41.667 | 4 | 5.250 | 0.200 | 30.000 | 0.000 | 3.000 |
| 34 | 30 | 31.957 | 38.043 | 4 | 5.250 | 0.200 | 0.000 | 30.000 | 3.000 |
| 35 | 10 | 47.143 | 42.857 | 5 | 5.250 | 0.200 | 30.000 | 25.000 | 3.000 |
| 36 | 15 | 96.905 | 88.095 | 5 | 5.250 | 0.200 | 30.000 | 20.000 | 3.000 |
| 37 | 30 | 31.957 | 38.043 | 5 | 5.250 | 0.200 | 0.000 | 30.000 | 3.000 |
| 38 | 10 | 35.455 | 54.545 | 6.5 | 5.250 | 0.700 | 30.000 | 0.000 | 3.000 |
| 39 | 15 | 84.457 | 100.543 | 6.5 | 5.250 | 0.700 | 30.000 | 30.000 | 3.000 |
| 40 | 30 | 89.048 | 80.952 | 6.5 | 5.250 | 0.700 | 30.000 | 30.000 | 3.000 |
| 41 | 10 | 41.087 | 48.913 | 4 | 5.250 | 0.700 | 30.000 | 30.000 | 3.000 |
| 42 | 15 | 45.280 | 39.720 | 4 | 5.250 | 0.700 | 0.000 | 0.000 | 3.000 |
| 43 | 30 | 107.500 | 62.500 | 4 | 5.250 | 0.700 | 30.000 | 30.000 | 3.000 |
| 44 | 5 | 77.243 | 67.757 | 4 | 5.250 | 0.700 | 0.000 | 15.000 | 3.000 |
| 45 | 15 | 45.280 | 39.720 | 5 | 5.250 | 0.700 | 0.000 | 20.000 | 3.000 |
| 46 | 30 | 90.561 | 79.439 | 5 | 5.250 | 0.700 | 0.000 | 30.000 | 3.000 |
| 47 | 10 | 47.944 | 42.056 | 5 | 5.250 | 0.700 | 0.000 | 10.000 | 3.000 |
| 48 | 5 | 50.607 | 44.393 | 5.5 | 5.250 | 0.700 | 30.000 | 0.000 | 3.000 |
| 49 | 30 | 107.500 | 62.500 | 5.5 | 5.250 | 0.700 | 30.000 | 0.000 | 3.000 |
| 50 | 10 | 47.944 | 42.056 | 5.5 | 5.250 | 0.700 | 30.000 | 30.000 | 3.000 |
| 51 | 15 | 46.364 | 38.636 | 4 | 5.250 | 0.200 | 30.000 | 25.000 | 3.000 |
| 52 | 15 | 46.364 | 38.636 | 4 | 5.250 | 0.200 | 0.000 | 20.000 | 3.000 |
| 53 | 10 | 46.098 | 43.902 | 5 | 5.250 | 0.200 | 15.000 | 30.000 | 3.000 |
| 54 | 15 | 43.537 | 41.463 | 5 | 5.250 | 0.200 | 30.000 | 0.000 | 3.000 |
| 55 | 10 | 45.000 | 45.000 | 5 | 5.250 | 0.200 | 0.000 | 30.000 | 3.000 |
| 56 | 10 | 59.492 | 30.508 | 6.5 | 5.250 | 0.200 | 30.000 | 30.000 | 3.000 |
| 57 | 15 | 39.054 | 45.946 | 6.5 | 5.250 | 0.200 | 0.000 | 0.000 | 3.000 |
| 58 | 30 | 35.854 | 34.146 | 6.5 | 5.250 | 0.200 | 30.000 | 0.000 | 3.000 |
| 59 | 10 | 50.000 | 40.000 | 6.5 | 5.250 | 0.700 | 30.000 | 30.000 | 3.000 |
| 60 | 10 | 38.571 | 51.429 | 6.5 | 5.250 | 0.700 | 30.000 | 30.000 | 3.000 |
| 61 | 7.5 | 41.954 | 50.546 | 6.5 | 5.250 | 0.700 | 30.000 | 30.000 | 3.000 |
| 62 | 10 | 42.632 | 47.368 | 6.5 | 5.250 | 0.700 | 30.000 | 30.000 | 3.000 |
| 63 | 10 | 46.098 | 43.902 | 6.5 | 5.250 | 0.700 | 30.000 | 30.000 | 3.000 |
| 64 | 10 | 39.721 | 50.279 | 6.5 | 5.250 | 0.700 | 30.000 | 30.000 | 3.000 |
| 65 | 5 | 44.198 | 50.802 | 6.5 | 5.250 | 0.700 | 30.000 | 30.000 | 3.000 |
| 66 | 2.5 | 46.453 | 51.047 | 6.5 | 5.250 | 0.700 | 30.000 | 30.000 | 3.000 |
| 67 | 5 | 51.221 | 43.779 | 6.5 | 5.250 | 0.700 | 30.000 | 30.000 | 3.000 |
| 68 | 2.5 | 54.167 | 43.333 | 6.5 | 5.250 | 0.700 | 30.000 | 30.000 | 3.000 |
| 69 | 10 | 66.440 | 23.560 | 6.5 | 5.250 | 0.700 | 30.000 | 30.000 | 3.000 |
| 70 | 10 | 66.440 | 23.560 | 6.5 | 5.250 | 0.700 | 30.000 | 30.000 | 3.000 |
| 71 | 10 | 66.440 | 23.560 | 6.5 | 5.250 | 0.700 | 30.000 | 30.000 | 3.000 |
| 72 | 10 | 40.000 | 50.000 | 6.5 | 5.250 | 0.700 | 30.000 | 30.000 | 3.000 |
| 73 | 10 | 40.000 | 50.000 | 6.5 | 5.250 | 0.700 | 30.000 | 30.000 | 3.000 |
| 74 | 10 | 40.000 | 50.000 | 5.5 | 0.000 | 0.700 | 30.000 | 30.000 | 3.000 |
| 75 | 10 | 40.000 | 50.000 | 6.5 | 5.250 | 0.700 | 30.000 | 30.000 | 3.000 |
| 76 | 10 | 40.000 | 50.000 | 6.5 | 5.250 | 0.700 | 30.000 | 30.000 | 3.000 |
| 77 | 10 | 40.000 | 50.000 | 6.5 | 5.250 | 0.700 | 30.000 | 30.000 | 3.000 |
| 78 | 10 | 66.440 | 23.560 | 6.5 | 5.250 | 0.700 | 30.000 | 30.000 | 3.000 |
| 79 | 10 | 66.440 | 23.560 | 6.5 | 5.250 | 0.700 | 30.000 | 30.000 | 3.000 |
| 80 | 10 | 40.000 | 50.000 | 5.5 | 0.000 | 0.700 | 30.000 | 30.000 | 3.000 |
| 81 | 10 | 40.000 | 50.000 | 5.5 | 5.250 | 0.700 | 30.000 | 30.000 | 3.000 |
| 82 | 10 | 44.444 | 55.556 | 5.5 | 5.250 | 0.700 | 30.000 | 30.000 | 3.000 |
| 83 | 10 | 66.440 | 23.560 | 5.5 | 5.250 | 0.700 | 30.000 | 30.000 | 3.000 |
| 84 | 10 | 54.000 | 36.000 | 4 | 5.250 | 0.700 | 30.000 | 30.000 | 3.000 |
| 85 | 10 | 50.000 | 40.000 | 4 | 5.250 | 0.700 | 30.000 | 30.000 | 3.000 |
| 86 | 12.5 | 48.611 | 38.889 | 4 | 5.250 | 0.700 | 30.000 | 30.000 | 3.000 |
| 87 | 15 | 46.575 | 38.425 | 4 | 5.250 | 0.700 | 30.000 | 30.000 | 3.000 |
| 88 | 15 | 46.575 | 38.425 | 4 | 5.250 | 0.700 | 30.000 | 30.000 | 3.000 |
| 89 | 15 | 46.575 | 38.425 | 4 | 5.250 | 0.700 | 30.000 | 30.000 | 3.000 |
| 90 | 10 | 50.000 | 40.000 | 4.5 | 5.250 | 0.700 | 30.000 | 30.000 | 3.000 |
| 91 | 30 | 94.444 | 75.556 | 4 | 5.250 | 0.700 | 30.000 | 30.000 | 3.000 |
| 92 | 15 | 46.712 | 38.288 | 4 | 5.250 | 0.700 | 30.000 | 30.000 | 3.000 |
| 93 | 12 | 48.889 | 39.111 | 4 | 5.250 | 0.700 | 30.000 | 30.000 | 3.000 |
| 94 | 10 | 39.721 | 50.279 | 6.5 | 5.250 | 0.700 | 30.000 | 30.000 | 3.000 |
| 95 | 10 | 90.000 | 0.000 | 6.5 | 5.250 | 0.700 | 30.000 | 30.000 | 3.000 |
| 96 | 15 | 46.575 | 38.425 | 4 | 0.000 | 0.700 | 0.000 | 0.000 | 3.000 |
| 97 | 15 | 46.575 | 38.425 | 4 | 0.000 | 0.700 | 0.000 | 0.000 | 3.000 |
| 98 | 15 | 54.643 | 30.357 | 4 | 5.250 | 0.700 | 0.000 | 0.000 | 3.000 |
| 99 | 10 | 39.72 | 50.279 | 6.5 | 5.250 | 0.700 | 30.000 | 30.000 | 3.000 |
| 100 | 10 | 90.00 | | 6.5 | 5.250 | 0.700 | 30.000 | 30.000 | 3.000 |
| 101 | 15 | 46.57 | 38.425 | 4 | | 0.700 | | | 3.000 |
| 102 | 15 | 46.75 | 38.425 | 4 | | 0.700 | | | 3.000 |
| 103 | 15 | 54.64 | 30.357 | 4 | | 0.700 | | | 3.000 |
| 104 | 6.1 | 46.575 | 38.425 | 6.5 | 5.250 | 0.700 | 0.000 | 30.000 | 3.000 |
| 105 | 6.1 | 64.516 | 35.484 | 6.5 | 5.250 | 0.700 | 0.000 | 30.000 | 3.000 |

TABLE 8-continued

Preferred Antifungal Formulations of the Invention

| 106 | 6.1 | 66.440 | 23.560 | 6.5 | 5.250 | 0.700 | 0.000 | 30.000 | 3.000 |
| 107 | 10 | 46.575 | 38.425 | 6.5 | 5.250 | 0.700 | 0.000 | 30.000 | 3.000 |
| 108 | 10 | 64.516 | 35.484 | 6.5 | 5.250 | 0.700 | 0.000 | 30.000 | 3.000 |
| 109 | 10 | 66.440 | 23.560 | 6.5 | 5.250 | 0.700 | 0.000 | 30.000 | 3.000 |

Table 8B: The table lists the specific components of the formulas listed above.

| Formula | Lipid | Surfactant | Buffer | Antimicrobial | Antioxidants | Emollient | Chelator | Other |
|---|---|---|---|---|---|---|---|---|
| 1-4 | Sphingomyelin, e.g., brain | Tween 80 | Lactate | Benzyl alcohol | BHT (0.200) sodium metabisulfite (0.500) | Glycerol | EDTA | Ethanol |
| 5-7 | Sphingomyelin, lauroyl | Brij 98 | Acetate | Benzyl alcohol | BHT (0.200) sodium metabisulfite (0.500) | Glycerol | EDTA | Ethanol |
| 8-12 | Phosphatidyl choline + Phosphatidylglycerol | Brij 98 | Phosphate | Benzyl alcohol | HTHQ | Glycerol | EDTA | Ethanol |
| 13-16 | Phosphatidyl choline + phosphatidylinositol | Span 20 | Acetate | Benzyl alcohol | HTHQ | Glycerol | EDTA | Ethanol |
| 17-20 | Phosphatidyl choline + phosphatidic acid | Tween 80 | Phosphate | Benzyl alcohol | BHT | Glycerol | EDTA | Ethanol |
| 21-28 | Phosphatidyl choline | Cremophor | Lactate | Thimerosal | BHA | Glycerol | EDTA | Ethanol |
| 29-31 | Phosphatidyl ethanolamine | Tween 80 | Phosphate | Thimerosal | BHT (0.200) sodium metabisulfite (0.500) | Glycerol | EDTA | Ethanol |
| 32-37 | Phosphatidyl glycerol | Brij 98 | Acetate | Benzyl alcohol | BHT | Glycerol | EDTA | Ethanol |
| 38-40 | Phosphatidyl ethanolamine | Cremophor | phosphate | Benzyl alcohol | BHT (0.200) sodium metabisulfite (0.500) | Glycerol | EDTA | Ethanol |
| 41-47 | Phosphatidyl glycerol | Tween 80 | Propionate | Benzyl alcohol | BHT (0.200) sodium metabisulfite (0.500) | Glycerol | EDTA | Ethanol |
| 48-50 | Phosphatidyl serine | Brij 98 | Phosphate | Thimerosal | BHT (0.200) sodium metabisulfite (0.500) | Glycerol | EDTA | Ethanol |
| 51-58 | Phosphatidyl glycerol | Brij 98 | Acetate | Benzyl alcohol | BHT | Glycerol | EDTA | Ethanol |
| 59-68 | Phosphatidyl choline | Tween 80 | Phosphate | Benzyl alcohol | BHT (0.200) sodium metabisulfite (0.500) | Glycerol | EDTA | Ethanol |
| 69-71 | Phosphatidyl choline | Brij 98 | Phosphate | Benzyl alcohol | BHT (0.200) sodium metabisulfite (0.500) | Glycerol | EDTA | Ethanol |
| 72-73 | Phosphatidyl choline | Tween 80 | Phosphate | Benzyl alcohol | BHT (0.200) sodium metabisulfite (0.500) | Glycerol | EDTA | Ethanol |
| 74 | Phosphatidyl choline | Tween 80 | Acetate | | BHT (0.200) sodium metabisulfite (0.500) | Glycerol | EDTA | Ethanol |
| 75 | Phosphatidyl choline | Tween 80 | Phosphate | Paraben | BHT (0.200) sodium metabisulfite (0.500) | Glycerol | EDTA | Ethanol |
| 76 | Phosphatidyl choline | Brij 98 | Phosphate | Benzalkonium chloride | BHT (0.200) sodium metabisulfite (0.500) | Glycerol | EDTA | Ethanol |
| 77 | Phosphatidyl choline | Tween 80 | Phosphate | Paraben | BHT (0.200) sodium metabisulfite (0.500) | Glycerol | EDTA | Ethanol |

TABLE 8-continued

Preferred Antifungal Formulations of the Invention

| # | | | | | | | | |
|---|---|---|---|---|---|---|---|---|
| 78 | Phosphatidyl choline | Brij 98 | Phosphate | Benzalkonium chloride | BHT (0.200) sodium metabisulfite (0.500) | Glycerol | EDTA | Ethanol |
| 79 | Phosphatidyl choline | Brij 98 | Phosphate | Benzyl alcohol | BHT (0.200) sodium metabisulfite (0.500) | Glycerol | EDTA | Ethanol |
| 80 | Phosphatidyl choline | Tween 80 | Acetate | | BHT (0.200) sodium metabisulfite (0.500) | Glycerol | EDTA | Ethanol |
| 81 | Phosphatidyl choline | Tween 80 | Acetate | Benzyl alcohol | BHT (0.200) sodium metabisulfite (0.500) | Glycerol | EDTA | Ethanol |
| 82-83 | Phosphatidyl choline | Tween 80 | Acetate | Benzyl alcohol | BHT (0.200) sodium metabisulfite (0.500) | Glycerol | EDTA | Ethanol |
| 84-88 | Phosphatidyl choline | Tween 80 | Acetate | Benzyl alcohol | BHA (0.200) sodium metabisulfite (0.500) | Glycerol | EDTA | Ethanol |
| 89 | Phosphatidyl choline | Tween 80 | Acetate | Benzyl alcohol | BHT (0.200) sodium metabisulfite (0.500) | Glycerol | EDTA | Ethanol |
| 90-93 | Phosphatidyl choline | Tween 80 | Acetate | Benzyl alcohol | BHT (0.200) sodium metabisulfite (0.500) | Glycerol | EDTA | Ethanol |
| 94 | Phosphatidyl choline | Tween 80 | Phosphate | Benzyl alcohol | BHT (0.200) sodium metabisulfite (0.500) | Glycerol | EDTA | Ethanol |
| 95 | Phosphatidyl choline | Tween 80 | Phosphate | Benzyl alcohol | BHT (0.200) sodium metabisulfite (0.500) | Glycerol | EDTA | Ethanol |
| 96-98 | Phosphatidyl choline | Tween 80 | Acetate | | BHT (0.200) sodium metabisulfite (0.500) | | EDTA | |
| 99 | Phosphatidyl choline | Tween 80 | Phosphate | Benzyl alcohol | BHT (0.200) sodium metabisulfite (0.500) | Glycerol | EDTA | Ethanol |
| 100 | Phosphatidyl choline | | Phosphate | Benzyl alcohol | BHT (0.200) sodium metabisulfite (0.500) | Glycerol | EDTA | Ethanol |
| 101-103 | Phosphatidyl choline | Tween 80 | Phosphate | | BHT (0.200) sodium metabisulfite (0.500) | | EDTA | |
| 104-109 | Phosphatidyl choline | Tween 80 | Phosphate | Benzyl Alcohol | BHT (0.200) sodium metabisulfite (0.500) | | EDTA | Ethanol |

Example Formulation 1

Formulation 1 comprises antifungal (10 mg/g), sphingomyelin (brain) (47.944 mg/g) as a lipid, Tween 80 (42.056 mg/g) as a surfactant, lactate buffer (pH 4), benzyl alcohol (5.250 mg/g) as an antimicrobial agent, BHT (0.200 mg/g) and sodium metabisulfite (0.0500 mg/g) as antioxidants, glycerol (30.000 mg/g), EDTA (3.000 mg/g) as a chelating agent, and ethanol (30.000 mg/g).

Example Formulation 2

Formulation 2 comprises antifungal (15 mg/g), sphingomyelin (brain) (53.750 mg/g) as a lipid, Tween 80 (31.250 mg/g) as a surfactant, lactate (pH 4) buffer, benzyl alcohol (5.250 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (15.000 mg/g).

Example Formulation 3

Formulation 3 comprises antifungal (30 mg/g), sphingomyelin (brain) (90.561 mg/g) as a lipid, Tween 80 (79.439 mg/g) as a surfactant, lactate (pH 4) buffer, benzyl alcohol (5.250 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 4

Formulation 4 comprises antifungal (10 mg/g), sphingomyelin (brain) (47.944 mg/g) as a lipid, Tween 80 (42.056 mg/g) as a surfactant, lactate (pH 5) buffer, benzyl alcohol (5.250 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 5

Formulation 5 comprises antifungal (5 mg/g), sphingomyelin lauroyl (50.607 mg/g) as a lipid, Brij 98 (44.393 mg/g) as a surfactant, acetate (pH 5) buffer, benzyl alcohol (5.250 mg/g) as an antimicrobial agent, BHT (0.200 mg/g) and sodium metabisulfite (0.500 mg/g) as antioxidants, EDTA (3.000 mg/g) as a chelating agent, and ethanol (10.000 mg/g).

Example Formulation 6

Formulation 6 comprises antifungal (30 mg/g), sphingomyelin lauroyl (90.561 mg/g) as a lipid, Brij 98 (79.439 mg/g) as a surfactant, acetate (pH 5) buffer, benzyl alcohol (5.250 mg/g) as antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 7

Formulation 7 comprises antifungal (7.5 mg/g), sphingomyelin lauroyl (49.276 mg/g) as a lipid, Brij 98 (79.439 mg/g) as a surfactant, acetate (pH 6.5) buffer, benzyl alcohol (5.250 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 8

Formulation 8 comprises antifungal (15 mg/g), phosphatidyl choline and phosphatidyl glycerol (53.750 mg/g) as a lipid, Brij 98 (31.250 mg/g) as a surfactant, phosphate (pH 6.5) buffer, benzyl alcohol (5.250 mg/g) as an antimicrobial agent, HTHQ (0.200 mg/g) as an antioxidant, glycerol (30.000 mg/g), and EDTA (3.000 mg/g) as a chelating agent.

Example Formulation 9

Formulation 9 comprises antifungal (30 mg/g), phosphatidyl choline and phosphatidyl glycerol (90.561 mg/g) as a lipid, Brij 98 (79.439 mg/g) as a surfactant, phosphate (pH 6.5) buffer, benzyl alcohol (5.250 mg/g) as an antimicrobial agent, HTHQ (0.200 mg/g) as antioxidant, glycerol (30.000 mg/g), EDTA (3.000 mg/g) as a chelating agent, and ethanol (30.000 mg/g).

Example Formulation 10

Formulation 10 comprises antifungal (10 mg/g), phosphatidyl choline and phosphatidyl glycerol (41.351 mg/g) as a lipid, Brij 98 (48.649 mg/g) as a surfactant, phosphate (pH 4) buffer, benzyl alcohol (5.250 mg/g) as an antimicrobial agent, HTHQ (0.200 mg/g) as an antioxidant, glycerol (30.000 mg/g), EDTA (3.000 mg/g) as a chelating agent, and ethanol (30.000 mg/g).

Example Formulation 11

Formulation 11 comprises antifungal (15 mg/g), phosphatidyl choline and phosphatidyl glycerol (47.882 mg/g) as a lipid, Brij 98 (37.118 mg/g) as a surfactant, phosphate (pH 4) buffer, benzyl alcohol (5.250 mg/g) as an antimicrobial agent, HTHQ (0.200 mg/g) as an antioxidant, glycerol, EDTA (3.000 mg/g) as a chelating agent, and ethanol (30.000 mg/g).

Example Formulation 12

Formulation 12 comprises antifungal (30 mg/g), phosphatidyl choline and phosphatidyl glycerol (95.764 mg/g) as a lipid, Brij 98 (74.236 mg/g) as a surfactant, phosphate (pH 4) buffer, benzyl alcohol (5.250 mg/g) as an antimicrobial agent, HTHQ (0.200 mg/g) as an antioxidant, glycerol (30.000 mg/g), EDTA (3.000 mg/g) as a chelating agent, and ethanol (30.000 mg/g).

Example Formulation 13

Formulation 13 comprises antifungal (10 mg/g), phosphatidyl choline and phosphatidylinositol (66.676 mg/g) as a lipid, Span 20 (24.324 mg/g) as a surfactant, acetate (pH 5) buffer, benzyl alcohol (5.250 mg/g), HTHQ (0.200 mg/g) as an antioxidant, EDTA (3.000 mg/g) as a chelating agent, and ethanol (25.000 mg/g).

Example Formulation 14

Formulation 14 comprises antifungal (15 mg/g), phosphatidyl choline and phosphatidylinositol (62.027 mg/g) as a lipid, Span 20 (22.973 mg/g) as a surfactant, acetate (pH 5) buffer, benzyl alcohol (5.250 mg/g) as an antimicrobial agent, HTHQ (0.200 mg/g) as an antioxidant, EDTA (3.000 mg/g) as a chelating agent, and ethanol (30.000 mg/g).

Example Formulation 15

Formulation 15 comprises antifungal (30 mg/g), phosphatidyl choline and phosphatidylinositol (124.054 mg/g) as a lipid, Span 20 (45.946 mg/g) as a surfactant, acetate (pH 5) buffer, benzyl alcohol (5.250 mg/g) as an antimicrobial agent, HTHQ (0.200 mg/g) as an antioxidant, glycerol (30.000 mg/g), and EDTA (3.000 mg/g) as a chelating agent, and ethanol (30.000 mg/g).

Example Formulation 16

Formulation 16 comprises antifungal (5 mg/g), phosphatidyl choline and phosphatidylinositol (62.687 mg/g) as a lipid, Span 20 (32.313 mg/g) as a surfactant, acetate (pH 6.5) buffer, benzyl alcohol (5.250 mg/g) as an antimicrobial agent, HTHQ (0.200 mg/g) as an antioxidant, glycerol (30.000 mg/g), EDTA (3.000 mg/g) as a chelating agent.

Example Formulation 17

Formulation 17 comprises antifungal (15 mg/g), phosphatidyl choline and phosphatidic acid (41.853 mg/g) as a lipid, Tween 80 (43.147 mg/g) as a surfactant, phosphate (pH 6.5) buffer, benzyl alcohol (5.250 mg/g) as an antimicrobial agent, BHT (0.200 mg/g) as an antioxidant, glycerol (30.000 mg/g), EDTA (3.000 mg/g), and ethanol (30.000 mg/g).

Example Formulation 18

Formulation 18 comprises antifungal (30 mg/g), phosphatidyl choline and phosphatidic acid (95.764 mg/g) as a lipid, Tween 80 (74.236 mg/g) as a surfactant, phosphate (pH 6.5) buffer, benzyl alcohol (5.250 mg/g) as an antimicrobial agent, BHT (0.200 mg/g) as an antioxidant, EDTA (3.000 mg/g), and ethanol (30.000 mg/g).

Example Formulation 19

Formulation 19 comprises antifungal (15 mg/g), phosphatidyl choline and phosphatidic acid (47.882 mg/g) as a lipid, Tween 80 (37.118 mg/g) as a surfactant, phosphate (pH 6.5) buffer, benzyl alcohol (5.250 mg/g) as an antimicrobial agent, BHT (0.200 mg/g) as an antioxidant, and EDTA (3.000 mg/g).

Example Formulation 20

Formulation 20 comprises antifungal (10 mg/g), phosphatidyl choline and phosphatidic acid (45.000 mg/g) as a lipid, Tween 80 (45.000 mg/g) as a surfactant, phosphate (pH 6.5) buffer, benzyl alcohol (5.250 mg/g) as an antimicrobial agent, BHT (0.200 mg/g) as antioxidant, and EDTA (3.000 mg/g).

Example Formulation 21

Formulation 21 comprises antifungal (10 mg/g), phosphatidyl choline (31.935 mg/g) as a lipid, cremophor (58.065 mg/g) as a surfactant, lactate (pH 5) buffer, thimerosal (5.250 mg/g) as an antimicrobial agent, BHA (0.200 mg/g) as an antioxidant, glycerol (30.000 mg/g), EDTA (3.000 mg/g) as a chelating agent, and ethanol (15.000 mg/g).

Example Formulation 22

Formulation 22 comprises antifungal (15 mg/g), phosphatidyl choline (42.500 mg/g) as a lipid, cremophor (42.500 mg/g) as a surfactant, lactate (pH 6.5) buffer, thimerosal (5.250 mg/g) as an antimicrobial agent, BHA (0.200 mg/g) as an antioxidant, glycerol (30.000 mg/g), and EDTA (3.000 mg/g) as a chelating agent.

Example Formulation 23

Formulation 23 comprises antifungal (10 mg/g), phosphatidyl choline (38.276 mg/g) as a lipid, cremophor (51.724 mg/g) as a surfactant, lactate (pH 4) buffer, thimerosal (5.250 mg/g) as an antimicrobial agent, BHA (0.200 mg/g) as an antioxidant, EDTA (3.000 mg/g) as a chelating agent, and ethanol (30.000 mg/g).

Example Formulation 24

Formulation 24 comprises antifungal (15 mg/g), phosphatidyl choline (42.500 mg/g) as a lipid, cremophor (42.500 mg/g) as a surfactant, lactate (pH 4) buffer, thimerosal (5.250 mg/g) as an antimicrobial agent, BHA (0.200 mg/g) as an antioxidant, EDTA (3.000 mg/g) as a chelating agent, and ethanol (15.000 mg/g).

Example Formulation 25

Formulation 25 comprises antifungal (30 mg/g), phosphatidyl choline (85.000 mg/g) as a lipid, cremophor (85.000 mg/g) as a surfactant, lactate (pH 4) buffer, thimerosal (5.250 mg/g) as an antimicrobial agent, BHA (0.200 mg/g) as an antioxidant, EDTA (3.000 mg/g) as a chelating agent, and ethanol (30.000 mg/g).

Example Formulation 26

Formulation 26 comprises antifungal (10 mg/g), phosphatidyl choline (38.276 mg/g) as a lipid, cremophor (51.276 mg/g) as a surfactant, lactate (pH 5) buffer, thimerosal (5.250 mg/g) as an antimicrobial agent, BHA (0.200 mg/g) as an antioxidant, and EDTA (3.000 mg/g) as a chelating agent.

Example Formulation 27

Formulation 27 comprises antifungal (15 mg/g), phosphatidyl choline (36.429 mg/g) as a lipid, cremophor (48.571 mg/g) as a surfactant, lactate (pH 5) buffer, thimerosal (5.250 mg/g) as an antimicrobial agent, BHA (0.200 mg/g) as an antioxidant, EDTA (3.000 mg/g) as a chelating agent, and ethanol (30.000 mg/g).

Example Formulation 28

Formulation 28 comprises antifungal (30 mg/g), phosphatidyl choline (72.299 mg/g) as a lipid, cremophor (97.701 mg/g) as a surfactant, lactate (pH 5) buffer, thimerosal (5.250 mg/g) as an antimicrobial agent, BHA (0.200 mg/g) as an antioxidant, EDTA (3.000 mg/g) as a chelating agent, and ethanol (15.000 mg/g).

Example Formulation 29

Formulation 29 comprises antifungal (7.5 mg/g), phosphatidyl ethanolamine (46.250 mg/g) as a lipid, Tween 80 (46.250 mg/g) as a surfactant, phosphate (pH 6.5) buffer, thimerosal (5.250 mg/g) as an antimicrobial agent, BHT (0.200 mg/g) and sodium metabisulfite (0.500 mg/g) as an antioxidant, EDTA (3.000 mg/g) as a chelating agent, and ethanol (20.000 mg/g).

Example Formulation 30

Formulation 30 comprises antifungal (15 mg/g), phosphatidyl ethanolamine (38.804 mg/g) as a lipid, Tween 80 (46.196 mg/g) as a surfactant, phosphate (pH 6.5) buffer, thimerosal (5.250 mg/g) as an antimicrobial agent, BHT (0.200 mg/g) and sodium metabisulfite (0.500 mg/g) as an antioxidant, glycerol (15.000 mg/g), EDTA (3.000 mg/g) as a chelating agent, and ethanol (30.000 mg/g).

Example Formulation 31

Formulation 31 comprises antifungal (30 mg/g), phosphatidyl ethanolamine (36.667 mg/g) as a lipid, Tween 80 (33.333 mg/g) as a surfactant, phosphate (pH 6.5) buffer, thimerosal (5.250 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 32

Formulation 32 comprises antifungal (10 mg/g), phosphatidyl glycerol (23.333 mg/g) as a lipid, Brij 98 (66.667 mg/g) as a surfactant, acetate (pH 4) buffer, benzyl alcohol (5.250 mg/g) as an antimicrobial agent, BHT (0.200 mg/g) as an antioxidant, and EDTA (3.000 mg/g) as a chelating agent.

Example Formulation 33

Formulation 33 comprises antifungal (12.5 mg/g), phosphatidyl glycerol (45.833 mg/g) as a lipid, Brij 98 (41.667 mg/g) as a surfactant, acetate (pH 4) buffer, benzyl alcohol (5.250 mg/g) as an antimicrobial agent, BHT (0.200 mg/g) as an antioxidant, glycerol (30.000 mg/g), and EDTA (3.000 mg/g) as a chelating agent.

Example Formulation 34

Formulation 34 comprises antifungal (30 mg/g), phosphatidyl glycerol (31.957 mg/g) as a lipid, Brij 98 (38.043 mg/g) as a surfactant, acetate (pH 4) buffer, benzyl alcohol (5.250 mg/g) as antimicrobial agent, BHT (0.200 mg/g) as an antioxidant, EDTA (3.000 mg/g) as a chelating agent, and ethanol (30.000 mg/g).

Example Formulation 35

Formulation 35 comprises antifungal (10 mg/g), phosphatidyl glycerol (47.143 mg/g) as a lipid, Brij 98 (42.857 mg/g) as a surfactant, acetate (pH 5) buffer, benzyl alcohol (5.250 mg/g) as an antimicrobial agent, BHT (0.200 mg/g) as an antioxidant, glycerol (30.000 mg/g), EDTA (3.000 mg/g) as a chelating agent, and ethanol (25.000 mg/g).

Example Formulation 36

Formulation 36 comprises antifungal (15 mg/g), phosphatidyl glycerol (96.905 mg/g) as a lipid, Brij 98 (88.095 mg/g) as a surfactant, acetate (pH 5) buffer, benzyl alcohol (5.250 mg/g) as an antimicrobial agent, BHT (0.200 mg/g) as an antioxidant, glycerol (30.000 mg/g), EDTA (3.000 mg/g) as a chelating agent, and ethanol (20.000 mg/g).

Example Formulation 37

Formulation 37 comprises antifungal (30 mg/g), phosphatidyl glycerol (31.957 mg/g) as a lipid, Brij 98 (38.043) as a surfactant, acetate (pH 5) buffer, benzyl alcohol (5.250 mg/g) as an antimicrobial agent, BHT (0.200 mg/g) as an antioxidant, EDTA (3.000 mg/g) as a chelating agent, and ethanol (30.000 mg/g).

Example Formulation 38

Formulation 38 comprises antifungal (10 mg/g), phosphatidyl ethanolamine (35.455 mg/g) as a lipid, cremophor (54.545 mg/g) as a surfactant, phosphate (pH 6.5) buffer, benzyl alcohol (5.250 mg/g) as an antimicrobial agent, BHT (0.200 mg/g) and sodium metabisulfite (0.500 mg/g) as antioxidants, glycerol (30.000 mg/g), and EDTA (3.000 mg/g) as a chelating agent.

Example Formulation 39

Formulation 39 comprises antifungal (15 mg/g), phosphatidyl ethanolamine (84.457 mg/g) as a lipid, cremophor (100.543 mg/g) as a surfactant, phosphate (pH 6.5) buffer, benzyl alcohol (5.250 mg/g) as an antimicrobial agent, BHT (0.200 mg/g) and sodium metabisulfite (0.500 mg/g) as antioxidants, EDTA (3.000 mg/g) as a chelating agent, and ethanol (30.000 mg/g).

Example Formulation 40

Formulation 40 comprises antifungal (30 mg/g), phosphatidyl ethanolamine (89.048 mg/g) as a lipid, cremophor (80.952 mg/g) as a surfactant, phosphate (pH 6.5) buffer, benzyl alcohol (5.250 mg/g), BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 41

Formulation 41 comprises antifungal (10 mg/g), phosphatidyl glycerol (41.087 mg/g) as a lipid, Tween 80 (48.913 mg/g) as a surfactant, propionate (pH 4) buffer, benzyl alcohol (5.250 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 42

Formulation 42 comprises antifungal (15 mg/g), phosphatidyl glycerol (45.280 mg/g) as a lipid, Tween 80 (39.720 mg/g) as a surfactant, propionate (pH 4) buffer, benzyl alcohol (5.250 mg/g) as an antimicrobial agent, BHT (0.200 mg/g) and sodium metabisulfite (0.500 mg/g), and EDTA (3.000 mg/g) as a chelating agent.

Example Formulation 43

Formulation 43 comprises antifungal (30 mg/g), phosphatidyl glycerol (107.500 mg/g) as a lipid, Tween 80 (62.500 mg/g) as a surfactant, propionate (pH 4) buffer, benzyl alcohol (5.250 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 44

Formulation 44 comprises antifungal (5 mg/g), phosphatidyl glycerol (77.243 mg/g) as a lipid, Tween 80 (67.757 mg/g) as a surfactant, propionate (pH 4) buffer, benzyl alcohol (5.250 mg/g) as an antimicrobial agent, BHT (0.200 mg/g) and sodium metabisulfite (0.500 mg/g) as antioxidants, EDTA (3.000 mg/g) as a chelating agent, and ethanol (30.000 mg/g).

Example Formulation 45

Formulation 45 comprises antifungal (15 mg/g), phosphatidyl glycerol (45.280 mg/g) as a lipid, Tween 80 (39.720 mg/g) as a surfactant, propionate (pH 5) buffer, benzyl alcohol (5.250 mg/g) as an antimicrobial agent, BHT (0.200 mg/g) and sodium metabisulfite (0.500 mg/g) as antioxidants, EDTA (3.000 mg/g) as a chelating agent, and ethanol (30.000 mg/g).

Example Formulation 46

Formulation 46 comprises antifungal (30 mg/g), phosphatidyl glycerol (90.561 mg/g) as a lipid, Tween 80 (79.439 mg/g) as a surfactant, propionate (pH 5) buffer, benzyl alcohol (5.250 mg/g) as an antimicrobial agent, BHT (0.200 mg/g) and sodium metabisulfite (0.500 mg/g) as antioxidants, EDTA (3.000 mg/g) as a chelating agent, and ethanol (30.000 mg/g).

Example Formulation 47

Formulation 47 comprises antifungal (10 mg/g), phosphatidyl glycerol (47.944 mg/g) as a lipid, Tween 80 (42.056 mg/g) as a surfactant, propionate (pH 5) buffer, benzyl alcohol (5.250 mg/g) as an antimicrobial agent, BHT (0.200 mg/g) and sodium metabisulfite (0.500 mg/g) as antioxidants, EDTA (3.000 mg/g) as a chelating agent, and ethanol (10.000 mg/g).

Example Formulation 48

Formulation 48 comprises antifungal (5 mg/g), phosphatidyl serine (50.607 mg/g) as a lipid, Brij 98 (44.393 mg/g) as a surfactant, phosphate (pH 5.5) buffer, thimerasol (5.250 mg/g) as an antimicrobial agent, BHT (0.200 mg/g) and sodium metabisulfite (0.500 mg/g) as antioxidants, glycerol (30.000 mg/g), and EDTA (3.000 mg/g) as a chelating agent.

Example Formulation 49

Formulation 49 comprises antifungal (30 mg/g), phosphatidyl serine (107.500 mg/g) as a lipid, Brij 98 (62.500 mg/g) as a surfactant, phosphate (pH 5.5) buffer, thimerasol (5.250 mg/g) as an antimicrobial agent, BHT (0.200 mg/g) and sodium metabisulfite (0.500 mg/g) as antioxidants, glycerol (30.000 mg/g), and EDTA (3.000 mg/g) as a chelating agent.

Example Formulation 50

Formulation 50 comprises antifungal (10 mg/g), phosphatidyl serine (47.944 mg/g) as a lipid, Brij 98 (42.056 mg/g) as a surfactant, phosphate (pH 5.5) buffer, thimerasol (5.250 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 51

Formulation 51 comprises antifungal (15 mg/g), phosphatidyl glycerol (46.364 mg/g) as a lipid, Brij 98 (38.636 mg/g) as a surfactant, acetate (pH 4) buffer, benzyl alcohol (5.250 mg/g) as an antimicrobial, BHT (0.200 mg/g) as an antioxidant, glycerol (30.000 mg/g), EDTA (3.000 mg/g) as a chelating agent, and ethanol (25.000 mg/g).

Example Formulation 52

Formulation 52 comprises antifungal (15 mg/g), phosphatidyl glycerol (46.364 mg/g) as a lipid, Brij 98 (38.636 mg/g) as a surfactant, acetate (pH 4) buffer, benzyl alcohol (5.250 mg/g) as an antimicrobial, BHT (0.200 mg/g) as an antioxidant, EDTA (3.000 mg/g) as a chelating agent, and ethanol (20.000 mg/g).

Example Formulation 53

Formulation 53 comprises antifungal (10 mg/g), phosphatidyl glycerol (46.098 mg/g) as a lipid, Brij 98 (43.902 mg/g) as a surfactant, acetate (pH 5) buffer, benzyl alcohol (5.250 mg/g) as an antimicrobial, BHT (0.200 mg/g) as an antioxidant, glycerol (15.000 mg/g), EDTA (3.000 mg/g) as a chelating agent, and ethanol (30.000 mg/g).

Example Formulation 54

Formulation 54 comprises antifungal (15 mg/g), phosphatidyl glycerol (43.537 mg/g) as a lipid, Brij 98 (41.463 mg/g) as a surfactant, acetate (pH 5) buffer, benzyl alcohol (5.250 mg/g) as an antimicrobial, BHT (0.200 mg/g) as an antioxidant, glycerol (30.000 mg/g), and EDTA (3.000 mg/g) as a chelating agent.

Example Formulation 55

Formulation 55 comprises antifungal (10 mg/g), phosphatidyl glycerol (45.000 mg/g) as a lipid, Brij 98 (45.000 mg/g) as a surfactant, acetate (pH 5) buffer, benzyl alcohol (5.250 mg/g) as an antimicrobial, BHT (0.200 mg/g) as an antioxidant, EDTA (3.000 mg/g) as a chelating agent, and ethanol (30.000 mg/g).

Example Formulation 56

Formulation 56 comprises antifungal (10 mg/g), phosphatidyl glycerol (59.492 mg/g) as a lipid, Brij 98 (30.508 mg/g) as a surfactant, acetate (pH 6.5) buffer, benzyl alcohol (5.250 mg/g) as an antimicrobial, BHT (0.200 mg/g) as an antioxidant, glycerol (30.000 mg/g), EDTA (3.000 mg/g) as a chelating agent, and ethanol (30.000 mg/g).

Example Formulation 57

Formulation 57 comprises antifungal (15 mg/g), phosphatidyl glycerol (39.054 mg/g) as a lipid, Brij 98 (45.946 mg/g) as a surfactant, acetate (pH 6.5) buffer, benzyl alcohol (5.250 mg/g) as an antimicrobial, BHT (0.200 mg/g) as an antioxidant, and EDTA (3.000 mg/g) as a chelating agent.

Example Formulation 58

Formulation 58 comprises antifungal (30 mg/g), phosphatidyl glycerol (35.854 mg/g) as a lipid, Brij 98 (34.146 mg/g) as a surfactant, acetate (pH 6.5) buffer, benzyl alcohol (5.250 mg/g) as an antimicrobial, BHT (0.200 mg/g) as an antioxidant, glycerol (30.000 mg/g), and EDTA (3.000 mg/g) as a chelating agent.

Example Formulation 59

Formulation 59 comprises antifungal (10 mg/g), phosphatidyl choline (50.000 mg/g) as a lipid, Tween 80 (40.000 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 60

Formulation 60 comprises antifungal (10 mg/g), phosphatidyl choline (38.571 mg/g) as a lipid, Tween 80 (51.429 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g), and ethanol (30.000 mg/g).

Example Formulation 61

Formulation 61 comprises antifungal (7.5 mg/g), phosphatidyl choline (41.954 mg/g) as phospholipid, Tween 80 (50.546 mg/g) as surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g), and ethanol (30.000 mg/g).

Example Formulation 62

Formulation 62 comprises antifungal (10 mg/g), phosphatidyl choline (42.632 mg/g) as a lipid, Tween 80 (47.368 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 63

Formulation 63 comprises antifungal (10 mg/g), phosphatidyl choline (46.098 mg/g) as a lipid, Tween 80 (43.902 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 64

Formulation 64 comprises antifungal (10 mg/g), phosphatidyl choline (39.721 mg/g) as a lipid, Tween 80 (50.279 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 65

Formulation 65 comprises antifungal (5 mg/g), phosphatidyl choline (44.198 mg/g) as a lipid, Tween 80 (50.802 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 66

Formulation 66 comprises antifungal (2.5 mg/g), phosphatidyl choline (46.453 mg/g) as a lipid, Tween 80 (51.047 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 67

Formulation 67 comprises antifungal (5 mg/g), phosphatidyl choline (51.221 mg/g) as a lipid, Tween 80 (43.779 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 68

Formulation 68 comprises antifungal (2.5 mg/g), phosphatidyl choline (54.167 mg/g) as a lipid, Tween 80 (43.333 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 69

Formulation 69 comprises antifungal (10 mg/g), phosphatidyl choline (66.440 mg/g) as a lipid, Brij 98 (23.560 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 69 is an emulsion.

Example Formulation 70

Formulation 70 comprises antifungal (10 mg/g), phosphatidyl choline (66.440 mg/g) as a lipid, Brij 98 (23.560 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 70 is a suspension.

Example Formulation 71

Formulation 71 comprises antifungal (10 mg/g), phosphatidyl choline (66.440 mg/g) as a lipid, Brij 98 (23.560 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 72

Formulation 72 comprises antifungal (10 mg/g), phosphatidyl choline (40.000 mg/g) as a lipid, Tween 80 (50.000 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 72 is an emulsion.

Example Formulation 73

Formulation 73 comprises antifungal (10 mg/g), phosphatidyl choline (40.000 mg/g) as a lipid, Tween 80 (50.000 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 73 is a suspension.

Example Formulation 74

Formulation 74 comprises antifungal (10 mg/g), phosphatidyl choline (40.000 mg/g) as a lipid, Tween 80 (50.000 mg/g) as a surfactant, acetate (pH 5.5) buffer, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 75

Formulation 75 comprises antifungal (10 mg/g), phosphatidyl choline (40.000 mg/g) as a lipid, Tween 80 (50.000 mg/g) as a surfactant, phosphate (pH 6.5) buffer, paraben (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 76

Formulation 76 comprises antifungal (10 mg/g), phosphatidyl choline (40.000 mg/g) as a lipid, Brij 98 (50.000 mg/g) as a surfactant, phosphate (pH 6.5) buffer, benzalkonium chloride (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 77

Formulation 77 comprises antifungal (10 mg/g), phosphatidyl choline (40.000 mg/g) as a lipid, Tween 80 (50.000 mg/g) as a surfactant, phosphate (pH 6.5) buffer, paraben (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 78

Formulation 78 comprises antifungal (10 mg/g), phosphatidyl choline (66.440 mg/g) as a lipid, Brij 98 (23.560 mg/g) as a surfactant, phosphate (pH 6.5) buffer, benzalkonium chloride (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 79

Formulation 79 comprises antifungal (10 mg/g), phosphatidyl choline (66.440 mg/g) as a lipid, Brij 98 (23.560 mg/g) as a surfactant, phosphate (pH 6.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 80

Formulation 80 comprises antifungal (10 mg/g), phosphatidyl choline (40.000 mg/g) as a lipid, Tween 80 (50.000 mg/g) as a surfactant, acetate (pH 5.5) buffer, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 81

Formulation 81 comprises antifungal (10 mg/g), phosphatidyl choline (40.000 mg/g) as a lipid, Tween 80 (50.000 mg/g) as a surfactant, acetate (pH 5.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 82

Formulation 82 comprises antifungal (10 mg/g), phosphatidyl choline (44.444 mg/g) as a lipid, Tween 80 (55.556 mg/g) as a surfactant, acetate (pH 5.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 83

Formulation 83 comprises antifungal (10 mg/g), phosphatidyl choline (66.440 mg/g) as a lipid, Tween 80 (23.560 mg/g) as a surfactant, acetate (pH 5.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 84

Formulation 84 comprises antifungal (10 mg/g), phosphatidyl choline (54.000 mg/g) as a lipid, Tween 80 (36.000 mg/g) as a surfactant, acetate (pH 4) buffer, benzyl alcohol (5.250 mg/g) as an antimicrobial, BHA (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 85

Formulation 85 comprises antifungal (10 mg/g), phosphatidyl choline (50.000 mg/g) as a lipid, Tween 80 (40.000 mg/g) as a surfactant, acetate (pH 4) buffer, benzyl alcohol (5.250 mg/g) as an antimicrobial, BHA (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 86

Formulation 86 comprises antifungal (12.5 mg/g), phosphatidyl choline (48.611 mg/g) as a lipid, Tween 80 (38.889 mg/g) as a surfactant, acetate (pH 4) buffer, benzyl alcohol (5.250 mg/g) as an antimicrobial, BHA (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 87

Formulation 87 comprises antifungal (15 mg/g), phosphatidyl choline (46.575 mg/g) as a lipid, Tween 80 (38.425 mg/g) as a surfactant, acetate (pH 4) buffer, benzyl alcohol (5.250 mg/g) as an antimicrobial, BHA (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 87 is an emulsion.

Example Formulation 88

Formulation 88 comprises antifungal (15 mg/g), phosphatidyl choline (46.575 mg/g) as a lipid, Tween 80 (38.425 mg/g) as a surfactant, acetate (pH 4) buffer, benzyl alcohol (5.250 mg/g) as an antimicrobial, BHA (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 88 is suspension.

Example Formulation 89

Formulation 89 comprises antifungal (15 mg/g), phosphatidyl choline (46.575 mg/g) as a lipid, Tween 80 (38.425 mg/g) as a surfactant, acetate (pH 4) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 90

Formulation 90 comprises antifungal (10 mg/g), phosphatidyl choline (50.000 mg/g) as a lipid, Tween 80 (40.000 mg/g) as a surfactant, acetate (pH 4.5) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 91

Formulation 91 comprises antifungal (30 mg/g), phosphatidyl choline (94.444 mg/g) as a lipid, Tween 80 (75.556 mg/g) as a surfactant, acetate (pH 4) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 92

Formulation 92 comprises antifungal (15 mg/g), phosphatidyl choline (46.712 mg/g) as a lipid, Tween 80 (38.288 mg/g) as a surfactant, acetate (pH 4) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 93

Formulation 93 comprises antifungal (12 mg/g), phosphatidyl choline (48.889 mg/g) as a lipid, Tween 80 (39.111 mg/g) as a surfactant, acetate (pH 4) buffer, benzyl alcohol (5.250 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 94

Formulation 94 comprises antifungal (10 mg/g), phosphatidyl choline (39.721 mg/g) as a lipid, Tween 80 (50.279 mg/g) as a surfactant, phosphate (pH 6.5) buffer, benzyl alcohol (5.25 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 95

Formulation 95 comprises antifungal (10 mg/g), phosphatidyl choline (90.000 mg/g) as a lipid, phosphate buffer (pH 6.5), benzyl alcohol as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 96

Formulation 96 comprises antifungal (15 mg/g), phosphatidyl choline (46.575 mg/g) as a lipid, Tween 80 (38.425 mg/g) as a surfactant, phosphate (pH 4) buffer, BHT (0.500 mg/g) and sodium metabisulfite (0.200 mg/g) as antioxidants, and EDTA (3.000 mg/g) as a chelating agent. Example formulation 96 is an emulsion.

Example Formulation 97

Formulation 97 comprises antifungal (15 mg/g), phosphatidyl choline (46.575 mg/g) as a lipid, Tween 80 (38.425 mg/g) as a surfactant, phosphate (pH 4) buffer, BHT (0.500 mg/g) and sodium metabisulfite (0.200 mg/g) as antioxidants, and EDTA (3.000 mg/g). Example formulation 97 is a suspension.

Example Formulation 98

Formulation 98 comprises antifungal (15 mg/g), phosphatidyl choline (54.643 mg/g) as a lipid, Tween 80 (30.357 mg/g) as a surfactant, phosphate (pH 4) buffer, BHA (0.500 mg/g) and sodium metabisulfite (0.200 mg/g) as antioxidants, and EDTA (3.000 mg/g) as a chelating agent.

Example Formulation 99

Formulation 99 comprises antifungal (10 mg/g), phosphatidyl choline (39.72 mg/g) as a lipid, Tween 80 (50.279 mg/g) as surfactant, phosphate (pH 6.5) buffer, benzyl alcohol (5.25 mg/g) as an antimicrobial, BHT (0.200 mg/g) and sodium metabisulfite (0.500 mg/g) as antioxidants, glycerol (30.000 mg/g) as emollient, EDTA (3.000 mg/g) as the chelating agent, and ethanol (30.000 mg/g).

Example Formulation 100

Formulation 100 comprises antifungal (10 mg/g), phosphatidyl choline (90.00 mg/g) as a lipid, phosphate (pH 6.5) buffer, benzyl alcohol as antimicrobial, BHT (0.200 mg/g) and sodium metabisulfite (0.500 mg/g) as antioxidants, glycerol (30.000 mg/g) as emollient, EDTA (3.000 mg/g) as the chelating agent, and ethanol (30.000 mg/g).

Example Formulation 101

Formulation 101 comprises antifungal (15 mg/g), phosphatidyl choline (46.57 mg/g) as a lipid, Tween 80 (38.425 mg/g) as a surfactant, phosphate (pH 4) buffer, BHT (0.500 mg/g) and sodium metabisulfite (0.200 mg/g) as antioxidants, and EDTA (3.000 mg/g) as the chelating agent. Formulation 101 is formulated as an emulsion.

Example Formulation 102

Formulation 102 comprises antifungal (15 mg/g), phosphatidyl choline (46.57 mg/g) as a lipid, Tween 80 (38.425 mg/g) as a surfactant, phosphate (pH 4) buffer, BHT (0.500 mg/g) and sodium metabisulfite (0.200 mg/g) as antioxidants, and EDTA (3.000 mg/g) as the chelating agent. Formulation 102 as a suspension.

Example Formulation 103

Formulation 103 comprises antifungal (15 mg/g), phosphatidyl choline (54.64 mg/g) as a lipid, Tween 80 (30.357 mg/g) as a surfactant, phosphate (pH 4) buffer, BHA (0.500 mg/g) and sodium metabisulfite (0.200 mg/g) as antioxidants, EDTA (3.000 mg/g) as the chelating agent.

Example Formulation 104

Formulation 104 comprises antifungal (6.1 mg/g), phosphatidyl choline (46.58 mg/g) as a lipid, Tween 80 (38.43 mg/g) as a surfactant, benzyl alcohol (5.25 mg/g) as an antimicrobial, phosphate (pH 6.5) buffer, EDTA (3.000 mg/g) as the chelating agent, ethanol (30.000 mg/g), and optionally BHA (0.500 mg/g) and sodium metabisulfite (0.200 mg/g) as antioxidants.

Example Formulation 105

Formulation 105 comprises antifungal (6.1 mg/g), phosphatidyl choline (64.52 mg/g) as a lipid, Tween 80 (35.484 mg/g) as a surfactant, benzyl alcohol (5.25 mg/g) as an antimicrobial, phosphate (pH 6.5) buffer, EDTA (3.000 mg/g) as the chelating agent, ethanol (30.000 mg/g), and optionally BHA (0.500 mg/g) and sodium metabisulfite (0.200 mg/g) as antioxidants.

Example Formulation 106

Formulation 106 comprises antifungal (6.1 mg/g), phosphatidyl choline (66.44 mg/g) as a lipid, Tween 80 (23.56 mg/g) as a surfactant, benzyl alcohol (5.25 mg/g) as an antimicrobial, phosphate (pH 6.5) buffer, EDTA (3.000 mg/g) as the chelating agent, ethanol (30.000 mg/g), and optionally BHA (0.500 mg/g) and sodium metabisulfite (0.200 mg/g) as antioxidants.

Example Formulation 107

Formulation 107 comprises antifungal (10 mg/g), phosphatidyl choline (46.58 mg/g) as a lipid, Tween 80 (38.43 mg/g) as a surfactant, benzyl alcohol (5.25 mg/g) as an antimicrobial, phosphate (pH 6.5) buffer, EDTA (3.000 mg/g) as the chelating agent, ethanol (30.000 mg/g), and optionally BHA (0.500 mg/g) and sodium metabisulfite (0.200 mg/g) as antioxidants.

Example Formulation 108

Formulation 105 comprises antifungal (10 mg/g), phosphatidyl choline (64.52 mg/g) as a lipid, Tween 80 (35.484 mg/g) as a surfactant, benzyl alcohol (5.25 mg/g) as an antimicrobial, phosphate (pH 6.5) buffer, EDTA (3.000 mg/g) as the chelating agent, ethanol (30.000 mg/g), and optionally BHA (0.500 mg/g) and sodium metabisulfite (0.200 mg/g) as antioxidants.

Example Formulation 109

Formulation 109 comprises antifungal (10 mg/g), phosphatidyl choline (66.44 mg/g) as a lipid, Tween 80 (23.56 mg/g) as a surfactant, benzyl alcohol (5.25 mg/g) as an antimicrobial, phosphate (pH 6.5) buffer, EDTA (3.000 mg/g) as the chelating agent, ethanol (30.000 mg/g), and optionally BHA (0.500 mg/g) and sodium metabisulfite (0.200 mg/g) as antioxidants.

Example Formulations 1 through 109 may also optionally include thickeners such as pectin, xanthan gum, HPMC gel, methylcellulose or carbopol. Example Formulations 1 through 103 may contain antifungal, salts of antifungal, or derivatives or analogs of terbinanfine.

Example Formulations 1 through 109 may be prepared using any antifungal disclosed herein, e.g., terbinafine, salts of terbinafine, or derivatives or analogs of terbinafine.

Example 2

In-Vivo Study of Antifungal Formulation Efficacy and Pharmacokinetics

The efficacy and pharmacokinetics of topical antifungal formulations containing terbinafine were studied for the treatment of onychomycosis. The first purpose of the study was to determine the mycological cure rate after 12 weeks of treatment with the terbinafine formulations disclosed herein. The terbinafine formulations were administered to each subject on two target areas, such that 3.0 mg terbinafine is delivered to each target area twice daily (b.i.d.) for 12 weeks of application. After 12 weeks of continuous application patients discontinued treatment. The target area was defined as a 20 cm² area on and around each infected toe nail. Two weeks after discontinuing treatment (week 14 of the study), nail specimens were examined microscopically, followed by mycological culture and evaluation.

5.1.1. Measurements for Evaluating the Mycological Cure Rate

The mycological cure rate is defined by negative microscopy of potassium hydroxide (KOH) samples and negative culture for dermatophytes.

Mycological samples are taken from the patients. A central laboratory is used for processing the mycological samples. Patients may have an additional screening visit if the KOH microscopy is positive and the culture is negative for dermatophytes so they can be recultured. If the result of repeat culture is positive for dermatophytes, the patient can be enrolled as long as he/she is within approximately 3 weeks from screening visit.

Specimen Collection

To collect nail clippings for analysis, a Mycotrans collection envelope was positioned under the nail. The target nail was clipped using a nail clipper as far back as possible from the free edge of the target toenail without excessive patient discomfort. The crumbling subungual debris from under the trimmed edge of the nail was collected by scraping. The hyperkeratotic nail bed and subungual debris was included in the sample. Samples were also collected from any discolored, dystrophic or brittle parts of the large target toenail.

A KOH wet mount microscopy and a mycological culture for dermatophytes of the target toenail specimen was performed on the mycological samples. Samples of clinical specimens were plated onto Selective agar for pathogenic fungi, Merck, Darmstadt, Germany (product no.: 1.10415.0001) in order to isolate and identify the following species: *T. rubrum, T. interdigitale, T. tonsurans*, and other pathogenic dermatophytes, as well as *C. albicans*, and *S. brevicaulis*. Plates were incubated at 28° C. for one to four weeks, examined weekly, and suspicious colonies are examined microscopically and/or bio chemically tested for identification.

The mycological cure rate was determined for 81 toe nails, 14-weeks after the initiation of treatments with terbinafine formulations, and two weeks after treatment was completed. Of the 81 infected toe nails, 73 demonstrated complete mycological cure, while 8 did not. A summary of the data is shown in Table 9.

TABLE 9

Mycological Cure Rate at 14-weeks
Exact Confidence Limits for Proportions

| Mycological cure (imputed) | N | % of Total | 90% CI Exact |
|---|---|---|---|
| yes | 73 | 90.12 | [82.88, 94.99] |
| no | 8 | 9.88 | [5.01, 17.12] |
| Total | 81 | 100.0 | |

5.1.2. Determination of Terbinafine Serum and Nail Tissue Concentrations

The pharmacokinetics of topical terbinafine formulations were studied as well. The purpose of this study was to determine the terbinafine concentration in the serum and in target nail tissue for subjects who were administered topical terbinafine formulations.

Blood samples (2.7 ml) for the determination of terbinafine concentrations in serum were taken before the first application (0 hour) and 0.5, 1, 2, 4, 8, and 12 hours after administration of a 6.0 mg dose of topical terbinafine. The sample 12 hours following the first administration was taken before the second daily administration of the topical terbinafine formulation.

Serum samples for terbinafine were analyzed by LC-MSMS. The internal standard used was naftifine. Samples were prepared by adding 50 μL serum to 50 μL methanol and 300 μL of internal standard solution (50 μg/L naftifine in 9:1 acetonitrile/methanol solution). The solution was allowed to stand for 5 minutes, and then subjected to centrifugation. After centrifugation, 50 μL of the supernatant was added to 450 μL of the mobile phase solution.

The serum concentrations were measured at day 1 and week 12 of the study. For all individuals at each time point test, the serum samples were shown to contain less than 1 ng/ml terbinafine at steady state and for all trough levels.

The concentration of terbinafine in target nails that were treated with the topical terbinafine formulations of the invention was also determined. The collected nail clippings were subjected to alkaline hydrolysis, followed by extraction with hexane. All samples were diluted 1:100. The terbinafine concentration was then determined by LC-MSMS. Nail samples that were collected for this study showed a mean value of 3.4 mg/g nail tissue (STD 2.9) at week 14 of the study, which was two weeks after the cessation of administration of the topical terbinafine formulation. The median value for the data collected at this time was 2.3 mg/g nail tissue and the geometric mean was 2.4 mg/g nail tissue.

5.1.3. Evaluation of the Clinical Cure

Clinical cure is defined by normal growth of the toe nails of at least 2 mm after 24 weeks using standard methods known in the art (see, e.g., Tavakkol, et. al. The American Journal of Geriatric Pharmacotherapy. 2006; 4: 1-13). For assessment of clinical cure rate the length of the nails from the visible proximal margin of nail is measured and evaluated whether and how many mm of the nail growth is normal. In case of a normal nail growth of 2 mm (at week 24) from the proximal margin the nail is considered to be cured.

5.1.4. Conclusion

These results demonstrate that the antifungal formulations disclosed herein, comprising one or more antifungal (e.g., terbinafine), a lipid and a surfactant, are effective in treating onychomycosis in a human subject when administered topically to the nail plate and the surrounding skin. The antifungal formulations are able to effectively provide greater than 90% mycological cure rate in human subjects suffering from onychomycosis. The topical antifungal formulations provide an effective treatment for onychomycosis where prior topical formulations of antifungals have demonstrated to be ineffective in successfully curing the nail infection.

The invention claimed is:

1. A pharmaceutical formulation suitable for topical delivery of terbinafine, comprising, in an aqueous solution, i) terbinafine or a pharmaceutically acceptable salt thereof in an amount ranging from about 0.5% to about 10% by weight, ii) a phospholipid in an amount ranging from about 4% to about 7% by weight, and iii) a non-ionic surfactant in an amount ranging from about 1% to about 4%, wherein the molar ratio of the phospholipid to the non-ionic surfactant is from about 1:1 to about 5:1, and wherein the phospholipid is a compound of Formula III:

$$R^1\text{—}CH_2\text{—}CHR^2\text{—}CR^3H\text{—}O\text{—}PHO_2\text{—}O\text{—}R^4 \quad \text{(III)}$$

or an anion thereof, wherein $R^1$ and $R^2$ are independently hydrogen, OH, acyl, alkyl, n-hydroxyacyl or n-hydroxyalkyl, or are derived from a fatty acid or a fatty alcohol, wherein $R^1$ and $R^2$ may also be branched, with one or more methyl groups, may be saturated or mono-, di-, or poly-unsaturated, and wherein $R^1$ and $R^2$ are not both hydrogen, OH, or $C_1$-$C_3$ alkyl; $R^3$ is hydrogen; and $R^4$ is hydrogen, a short-chain alkyl group substituted by a tri-short-chain alkylammonium group, an amino-substituted short-chain alkyl group, serine, glycerol, or inositol.

2. The pharmaceutical formulation of claim 1, wherein the amount of terbinafine or a pharmaceutically acceptable salt thereof is about 1.5% by weight.

3. The pharmaceutical formulation of claim 1, wherein the aqueous solution is buffered at a pH in the range from pH 4 to pH 7.5.

4. The pharmaceutical formulation of claim 1, wherein the non-ionic surfactant is a polyoxyethylene sorbitan, a polyhydroxyethylene stearate, or a polyydroxyethylene-lauryl ether.

5. The pharmaceutical formulation of claim 1, wherein the non-ionic surfactant is polysorbate 80.

6. A pharmaceutical formulation suitable for topical delivery of terbinafine, comprising, in an aqueous solution, i) terbinafine or a pharmaceutically acceptable salt thereof in an amount ranging from about 0.5% to about 10% by weight, ii) a phospholipid in an amount ranging from about 4% to about 7% by weight, and iii) a non-ionic surfactant in an amount ranging from about 1% to about 4%, wherein the molar ratio of the phospholipid to the non-ionic surfactant is from about 1:1 to about 5:1, and wherein the phospholipid is a phosphatidylcholine.

7. The pharmaceutical formulation of claim 6, wherein the non-ionic surfactant is polysorbate 80.

8. The pharmaceutical formulation of claim 1, wherein the formulation comprises vesicles or extended surface aggregates.

9. The pharmaceutical formulation of claim 1, wherein the formulation comprises deformable vesicles capable of penetrating a barrier with pores having an average pore diameter at least 50% smaller than the average vesicle diameter before the penetration.

10. The pharmaceutical formulation of claim 1, wherein the pharmaceutical formulation is suitable for topical delivery to a nail.

11. The pharmaceutical formulation of claim 1, wherein the formulation further comprises one or more of a thickener, an antioxidant, or an antimicrobial.

12. A method for treating a fungal infection in a human subject comprising topically administering to the subject a pharmaceutical formulation comprising, in an aqueous solution, i) terbinafine or a pharmaceutically acceptable salt thereof in an amount ranging from about 0.5% to about 10% by weight, ii) a phospholipid in an amount ranging from about 4% to about 7% by weight, and iii) a non-ionic surfactant in an amount ranging from about 1% to about 4%, wherein the molar ratio of the phospholipid to the non-ionic surfactant is from about 1:1 to about 5:1, and wherein the phospholipid is a compound of Formula III:

$$R^1-CH_2-CHR^2-CR^3H-O-PHO_2-O-R^4 \qquad (III)$$

or an anion thereof, wherein $R^1$ and $R^2$ are independently hydrogen, OH, acyl, alkyl, n-hydroxyacyl or n-hydroxyalkyl, or are derived from a fatty acid or a fatty alcohol, wherein $R^1$ and $R^2$ may also be branched, with one or more methyl groups, may be saturated or mono-, di-, or poly-unsaturated, and wherein $R^1$ and $R^2$ are not both hydrogen, OH, or $C_1$-$C_3$ alkyl; $R^3$ is hydrogen; and $R^4$ is hydrogen, a short-chain alkyl group substituted by a tri-short-chain alkylammonium group, an amino-substituted short-chain alkyl group, serine, glycerol, or inositol.

13. The method of claim 12, wherein the non-ionic surfactant is polysorbate 80.

14. The method of claim 12, the phospholipid is a phosphatidylcholine.

15. The method of claim 12, wherein the fungal infection is a nail fungal infection.

16. The method of claim 12, wherein the fungal infection is onychomycosis.

17. The method of claim 12, wherein said topically administering comprises applying said formulation to the subject's nail and/or surrounding skin.

18. The pharmaceutical formulation of claim 1, wherein the formulation causes negative microscopy of potassium hydroxide samples and negative culture for dermatophytes in greater than 90% of infected toenails upon 14 weeks of administration to a human subject.

19. The pharmaceutical formulation of claim 18, wherein the non-ionic surfactant is polysorbate 80.

20. The pharmaceutical formulation of claim 18, the phospholipid is a phosphatidylcholine.

* * * * *